United States Patent
Osaka et al.

(10) Patent No.: US 9,882,138 B2
(45) Date of Patent: Jan. 30, 2018

(54) ORGANIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Harue Osaka, Kanagawa (JP); Kaori Ogita, Kanagawa (JP); Nobuharu Ohsawa, Tochigi (JP); Hiromi Seo, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 321 days.

(21) Appl. No.: 13/860,055

(22) Filed: Apr. 10, 2013

(65) Prior Publication Data

US 2013/0277653 A1    Oct. 24, 2013

(30) Foreign Application Priority Data

Apr. 20, 2012    (JP) .................................. 2012-096888

(51) Int. Cl.
*H01L 51/00* (2006.01)
*C07D 209/86* (2006.01)
(Continued)

(52) U.S. Cl.
CPC ........ *H01L 51/0052* (2013.01); *C07D 209/86* (2013.01); *C09K 11/06* (2013.01);
(Continued)

(58) Field of Classification Search
None
See application file for complete search history.

(56) References Cited

U.S. PATENT DOCUMENTS

| 5,840,217 A | 11/1998 | Lupo et al. |
| 6,406,804 B1 | 6/2002 | Higashi et al. |

(Continued)

FOREIGN PATENT DOCUMENTS

| CN | 1582073 A | 2/2005 |
| CN | 1634864 A | 7/2005 |

(Continued)

OTHER PUBLICATIONS

Machine English translation of Maki et al. (JP 2005-085599 A).*

(Continued)

*Primary Examiner* — J. L. Yang
(74) *Attorney, Agent, or Firm* — Husch Blackwell LLP

(57) ABSTRACT

A novel organic compound with which the emission characteristics, emission efficiency, and reliability of a light-emitting element can be improved; a light-emitting element including the organic compound; and a light-emitting device, an electronic device, and a lighting device each including the light-emitting element. The light-emitting element includes a hole-transport layer and a light-emitting layer between a pair of electrodes. At least one of the hole-transport layer and the light-emitting layer includes an organic compound having a skeleton represented by General Formula (G0).

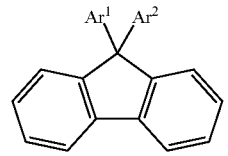

(G0)

15 Claims, 21 Drawing Sheets

(51) Int. Cl.
*C09K 11/06* (2006.01)
*H05B 33/14* (2006.01)
*H01L 51/50* (2006.01)

(52) U.S. Cl.
CPC ......... *H01L 51/0072* (2013.01); *H05B 33/14* (2013.01); *C09K 2211/1007* (2013.01); *C09K 2211/1011* (2013.01); *C09K 2211/1029* (2013.01); *H01L 51/0068* (2013.01); *H01L 51/0085* (2013.01); *H01L 51/5056* (2013.01); *H01L 2251/308* (2013.01)

(56) References Cited

U.S. PATENT DOCUMENTS

| | | | |
|---|---|---|---|
| 6,822,094 | B2 | 11/2004 | Salbeck et al. |
| 6,887,392 | B2 | 5/2005 | Ogino et al. |
| 7,189,877 | B2 | 3/2007 | Nishiyama et al. |
| 7,208,869 | B2 | 4/2007 | Ogino et al. |
| 7,227,027 | B2 | 6/2007 | Qiu et al. |
| 7,273,663 | B2 | 9/2007 | Liao et al. |
| 7,303,937 | B2 | 12/2007 | Chen et al. |
| 7,326,474 | B2 | 2/2008 | Kim |
| 7,488,849 | B2 | 2/2009 | Kawakami |
| 7,540,978 | B2 | 6/2009 | Pfeiffer et al. |
| 7,547,562 | B2 | 6/2009 | Ogino |
| 7,550,173 | B2 | 6/2009 | Seo et al. |
| 7,816,668 | B2 | 10/2010 | Kawakami et al. |
| 7,897,964 | B2 | 3/2011 | Kawakami et al. |
| 7,952,093 | B2 | 5/2011 | Yamazaki et al. |
| 8,034,466 | B2 | 10/2011 | Sakata et al. |
| 8,304,094 | B2 | 11/2012 | Ohsawa et al. |
| 8,361,638 | B2 | 1/2013 | Stoessel et al. |
| 8,389,735 | B2 | 3/2013 | Murata et al. |
| 8,394,510 | B2 | 3/2013 | Mizuki et al. |
| 8,399,108 | B2 | 3/2013 | Yu et al. |
| 8,530,063 | B2 | 9/2013 | Kim et al. |
| 8,586,973 | B2 | 11/2013 | Martin et al. |
| 8,786,181 | B2 | 7/2014 | Eberle et al. |
| 2002/0093283 | A1 | 7/2002 | Seo et al. |
| 2004/0110958 | A1 | 6/2004 | Nishiyama et al. |
| 2006/0063027 | A1 | 3/2006 | Vestweber et al. |
| 2006/0180812 | A1 | 8/2006 | Sakata et al. |
| 2007/0003785 | A1 | 1/2007 | Slusarek et al. |
| 2007/0116984 | A1 | 5/2007 | Park et al. |
| 2008/0036365 | A1 | 2/2008 | Miki et al. |
| 2008/0199726 | A1 | 8/2008 | Schafer et al. |
| 2009/0160323 | A1 | 6/2009 | Nomura et al. |
| 2009/0174321 | A1 | 7/2009 | Osaka et al. |
| 2010/0301744 | A1 | 12/2010 | Osaka et al. |
| 2010/0308754 | A1 | 12/2010 | Gough et al. |
| 2011/0089816 | A1 | 4/2011 | Yokoyama et al. |
| 2011/0147728 | A1 | 6/2011 | Kawakami et al. |
| 2011/0220881 | A1 | 9/2011 | Yokoyama et al. |
| 2011/0272685 | A1 | 11/2011 | Parham et al. |
| 2012/0161107 | A1 | 6/2012 | Yokoyama et al. |
| 2013/0228767 | A1* | 9/2013 | Ludemann ............ C09K 11/06 257/40 |

FOREIGN PATENT DOCUMENTS

| | | | | |
|---|---|---|---|---|
| CN | | 1769269 | A | 5/2006 |
| CN | | 101903345 | A | 12/2010 |
| CN | | 102272264 | A | 12/2011 |
| EP | | 1 400 578 | A1 | 3/2004 |
| EP | | 2 206 716 | A1 | 7/2010 |
| JP | | 7-301928 | | 11/1995 |
| JP | | 2003-261472 | | 9/2003 |
| JP | | 2004-87395 | | 3/2004 |
| JP | | 2005-85599 | | 3/2005 |
| JP | | 2005-085599 | | 3/2005 |
| JP | | 2005-120030 | | 5/2005 |
| JP | | 2005-162660 | | 6/2005 |
| JP | | 2006-93284 | | 4/2006 |
| JP | | 2009-167175 | | 7/2009 |
| JP | | 2014-506392 | | 3/2014 |
| WO | WO 2008/147110 | A2 | | 12/2008 |
| WO | WO 2009/061314 | A1 | | 5/2009 |
| WO | WO 2010/043693 | A1 | | 4/2010 |
| WO | WO 2011/049325 | A2 | | 4/2011 |
| WO | WO-2011/049325 | A2 * | | 4/2011 |
| WO | WO-2012/048778 | A1 * | | 4/2012 ............ C09K 11/06 |
| WO | WO-2013/027846 | A1 * | | 2/2013 |

OTHER PUBLICATIONS

Van Slyke, S.A. et al. "Organic Electroluminescent Devices with Improved Stability," Applied Physics Letters, vol. 69, No. 15, Oct. 7, 1996, pp. 2160-2162.

Tsutsui, T. et al, "High Quantum Efficiency in Organic Light-Emitting Devices with Iridium-Complex as a Triplet Emissive Center," Japanese Journal of Applied Physics, vol. 38, part 2, No. 12B, Dec. 15, 1999, pp. L1502-L1504.

Adachi, C. et al, "High-Efficiency Red Electrophosphorescence Devices," Applied Physics Letters, vol. 78, No. 11, Mar. 12, 2001, pp. 1622-1624.

Thomas, K.R.J. et al., "Green and Yellow Electroluminescent Dipolar Carbazole Derivatives: Features and Benefits of Electron-Withdrawing Segments," Chemistry of Materials, vol. 14, No. 9, 2002, pp. 3852-3859.

Goldsmith, C.R. et al., "C-H Bond Activation by a Ferric Methoxide Complex: Modeling the Rate-Determining Step in the Mechanism of Lipoxygenase," Journal of the American Chemical Society, vol. 124, No. 1, 2002, pp. 83-96.

Thomas, K.R.J. et al, "New Carbazole-Oxadiazole Dyads for Electroluminescent Devices: Influence of Acceptor Substituents on Luminescent and Thermal Properties," Chemistry of Materials, vol. 16, No. 25, 2004, pp. 5437-5444.

Onishi, T. et al, "A Method of Measuring an Energy Level," *High Molecular EL Materials—Development of Light-Emitting High Molecular Compounds*, Kyoritsu Shuppan, Dec. 25, 2004, pp. 64-67 (with English Translation, pp. 1-3).

Kafafi, Z., *Organic Electroluminescence*, CRC Press, Taylor & Francis Group, LLC, 2005, pp. 152-161.

Shen, J. Y. et al, "High $T_g$ Blue Emitting Materials for Electroluminescent Devices," Journal of Materials Chemistry, The Royal Society of Chemistry, vol. 15, No. 25, 2005, pp. 2455-2463.

Shih, P.-I. et al, "A Novel Fluorene-Triphenylamine Hybrid That is a Highly Efficient Host Material for Blue-,Green-, and Red-Light-Emitting Electrophosphorescent Devices," Advanced Functional Materials, vol. 17, 2007, pp. 3514-3520.

Hou, X.-Y. et al, "Stable Hole-Transporting Molecular Glasses Based on Complicated 9,9-diarylfluorenes (CDAFs)," Synthetic Metals, vol. 159, 2009, pp. 1055-1060.

Chinese Office Action re Application No. CN 201310139145.5, dated Apr. 27, 2016.

Chinese Office Action re Application No. CN 201310139145.5, dated Oct. 28, 2016.

Yu, D.D et al., "Ternary Ambipolar Phosphine Oxide Hosts Based on Indirect Linkage for Highly Efficient Blue Electrophosphorescence: Towards High Triplet Energy, Low Driving Voltage and Stable Efficiencies," Advanced Materials, Jan. 24, 2012, vol. 24, No. 4, pp. 509-514.

\* cited by examiner

- - fluorescence spectrum of first/second organic compound 213/214
- - - phosphorescence spectrum of first/second organic compound 213/214
—— absorption spectrum of third organic compound 215
—— emission spectrum of exciplex

ORGANIC COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to an organic compound and a light-emitting element including the organic compound. The present invention also relates to a light-emitting device, an electronic device, and a lighting device each including the light-emitting element.

2. Description of the Related Art

In recent years, research and development have been extensively conducted on light-emitting elements using electroluminescence (EL). In a basic structure of such a light-emitting element, a layer containing a light-emitting substance is interposed between a pair of electrodes. By applying voltage to this element, light emission from the light-emitting substance can be obtained.

Such a light-emitting element is a self-luminous element and has advantages over liquid crystal displays, such as high visibility of pixels and no need of backlight; thus, such a light-emitting element is thought to be suitable as a flat panel display element. Besides, such a light-emitting element has advantages in that it can be manufactured to be thin and lightweight, and has very fast response speed.

Furthermore, since such a light-emitting element can be formed in a film form, planar light emission can be easily obtained; thus, a large-area element utilizing planar light emission can be formed. This feature is difficult to obtain with point light sources typified by incandescent lamps and LEDs or linear light sources typified by fluorescent lamps. Thus, the light-emitting element also has great potential as a planar light source applicable to a lighting device and the like.

Light-emitting elements utilizing electroluminescence are broadly classified according to whether they use an organic compound or an inorganic compound as a light-emitting substance. In the case where an organic compound is used as a light-emitting substance, application of voltage to a light-emitting element causes injection of electrons and holes from a pair of electrodes into a layer including the light-emitting organic compound, and thus current flows. The light-emitting organic compound is excited by the injection of carriers (electrons and holes), and emits light in returning to a ground state from the excited state (electrons and holes are recombined). The excited state formed by an organic compound can be a singlet excited state or a triplet excited state. Light emission from the singlet excited state is called fluorescence, and emission from the triplet excited state is called phosphorescence.

In improving element characteristics of such a light-emitting element, there are many problems which depend on substances used for the light-emitting element. Therefore, improvement in an element structure, development of a substance, and the like have been carried out in order to solve the problems. For example, a light-emitting element for which a compound that has a carbazole skeleton and an anthracene skeleton including a substituted or unsubstituted phenyl group and has an excellent carrier-transport property is used is disclosed (see Patent Document 1).

REFERENCE

Patent Document

[Patent Document 1]
Japanese Published Patent Application No. 2009-167175

SUMMARY OF THE INVENTION

Although development of materials used for light-emitting elements has progressed as reported in Patent Document 1, there is room for improvement in many aspects of, for example, emission characteristics, emission efficiency, and reliability; thus, development for more excellent light-emitting elements has been needed.

In view of the above, an object of one embodiment of the present invention is to provide a novel organic compound with which the emission characteristics, emission efficiency, and reliability of a light-emitting element can be improved. Another object is to provide a light-emitting element including the organic compound. Other objects are to provide a light-emitting device, an electronic device, and a lighting device each including the light-emitting element.

One embodiment of the present invention is a light-emitting element including at least a hole-transport layer and a light-emitting layer between a pair of electrodes. At least one of the hole-transport layer and the light-emitting layer includes an organic compound having a skeleton represented by General Formula (G0). Furthermore, the organic compound having the skeleton represented by General Formula (G0) is one embodiment of the present invention.

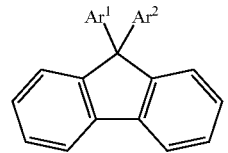

(G0)

In General Formula (G0), $Ar^1$ and $Ar^2$ are each independently any one of a phenyl group, a biphenyl group, and a group in which 3 to 6 benzene rings are bonded at the meta-positions; $Ar^1$ has a substituent and the substituent has a carbazole skeleton; and $Ar^2$ is unsubstituted.

A hole-transport layer is provided in an EL layer and the material for the hole-transport layer or the thickness of the hole-transport layer is adjusted, whereby the balance of holes which are transported to the light-emitting layer can be adjusted. As a result, the balance between electrons and holes which are transported to the light-emitting layer (what is called carrier balance) is adjusted, leading to improvement in the emission efficiency of a light-emitting element. Note that an organic compound, which is one embodiment of the present invention and has a skeleton represented by General Formula (G0), is a material having a high hole-transport property, so that the organic compound can be used for the hole-transport layer, the light-emitting layer, or both.

In the above-described structure, it is preferable that $Ar^1$ and $Ar^2$ be each independently a phenyl group or a biphenyl group. In addition, the substituent is preferably a substituted or unsubstituted N-carbazolyl group.

Another embodiment of the present invention is an organic compound represented by General Formula (G1).

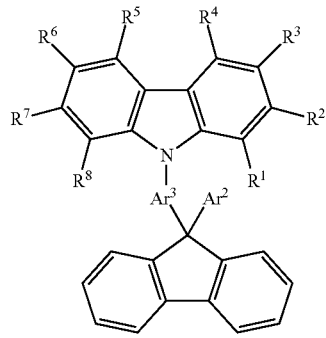

(G1)

In General Formula (G1), $Ar^2$ and $Ar^3$ are each independently any one of a phenyl group, a biphenyl group, and a group in which 3 to 6 benzene rings are bonded at the meta-positions; and $Ar^2$ is unsubstituted. In addition, $R^1$ to $R^8$ are each independently any one of hydrogen, an alkyl group having 1 to 12 carbon atoms, a substituted or unsubstituted phenyl group, and a substituted or unsubstituted biphenyl group.

In the above-described structure, it is preferale that $Ar^2$ be a phenyl group or a biphenyl group and $Ar^3$ be a phenylene group or a biphenyldiyl group. It is more preferable that $Ar^3$ be a metaphenylene group or a biphenyl-3,3'-diyl group.

Other embodiments of the present invention are organic compounds represented by Structural Formulae (G2-1), (G2-2), and (G3).

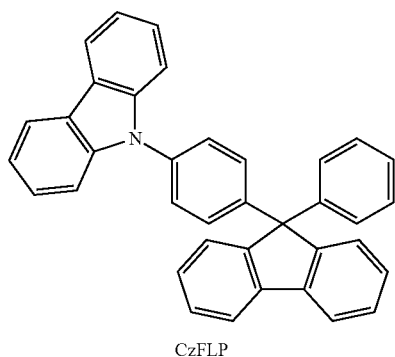

CzFLP (G2-1)

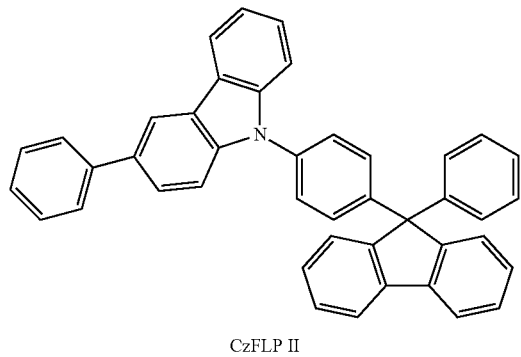

CzFLP II (G2-2)

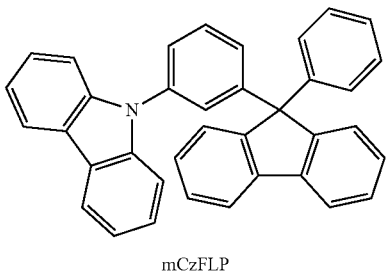

mCzFLP (G3)

A light-emitting device including the light-emitting element and an electronic device and a lighting device each including the light-emitting device are also included in the scope of one embodiment of the present invention. That is, the light-emitting device in this specification refers to an image display device, or a light source (including a lighting device). In addition, the light-emitting device includes, in its category, all of a module in which a connector such as a flexible printed circuit (FPC) or a tape carrier package (TCP) is connected to a light-emitting device, a module in which a printed wiring board is provided on the tip of a TCP, and a module in which an integrated circuit (IC) is directly mounted on a light-emitting element by a chip on glass (COG) method.

According to embodiments of the present invention, a novel organic compound with which the emission efficiency and reliability of a light-emitting element can be improved can be provided. Furthermore, a light-emitting element including the organic compound can be provided. Furthermore, a light-emitting device, an electronic device, and a lighting device each including the light-emitting element can be provided.

DETAILED DESCRIPTION OF THE INVENTION

Hereinafter, embodiments of the present invention will be described in detail with reference to the accompanying drawings. Note that the present invention is not limited to the following description, and it will be easily understood by those skilled in the art that the mode and detail can be modified in various ways without departing from the spirit and scope of the present invention. Therefore, the present invention should not be construed as being limited to the description in the following embodiments.

(Embodiment 1)

In this embodiment, a structure where an EL layer is provided between a pair of electrodes, and the EL layer includes at least a hole-transport layer and a light-emitting layer will be described with reference to FIG. 1.

Figure 1:
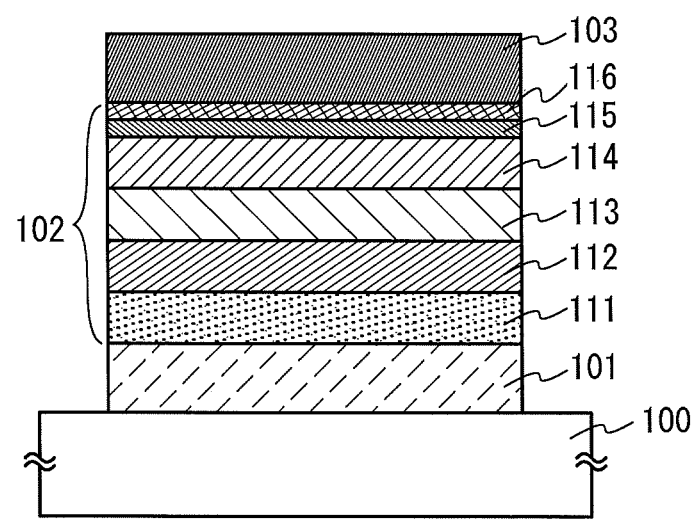
FIG. 1 illustrates a light-emitting element of one embodiment of the present invention.

In a light-emitting element described in this embodiment, as illustrated in FIG. 1, an EL layer 102 including a hole-transport layer 112 and a light-emitting layer 113 is provided between a pair of electrodes (a first electrode 101 and a second electrode 103), and the EL layer 102 includes a hole-injection layer 111, an electron-transport layer 114, an electron-injection layer 115, a charge-generation layer 116, and the like in addition to the hole-transport layer 112 and the light-emitting layer 113. Note that in this embodiment, the first electrode 101 is used as an anode and the second electrode 103 is used as a cathode.

It is preferable that at least one of the hole-transport layer 112 and the light-emitting layer 113 include an organic compound having a skeleton represented by General Formula (G0).

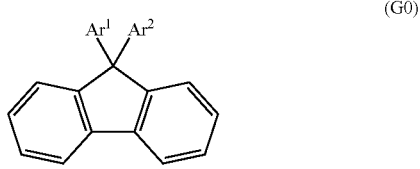

(G0)

In General Formula (G0), $Ar^1$ and $Ar^2$ are each independently any one of a phenyl group, a biphenyl group, and a group in which 3 to 6 benzene rings are bonded at the meta-positions; $Ar^1$ has a substituent and the substituent has a carbazole skeleton; and $Ar^2$ is unsubstituted. With $Ar^1$ having the above structure, a hole-transport material having high triplet-excitation energy level and high heat resistance can be obtained. Furthermore, with $Ar^2$ that is unsubstituted, the reliability of the element can be enhanced.

In General Formula (G0), it is preferable in view of triplet-excitation energy level that $Ar^1$ and $Ar^2$ be each independently a phenyl group or a biphenyl group. In addition, it is more preferable that the substituent be a substituted or unsubstituted N-carbazolyl group.

The hole-injection layer 111 included in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge-generation layer 116 is a layer containing a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114.

A specific example in which the light-emitting element described in this embodiment is manufactured is described below.

The substrate 100 is used as a support of the light-emitting element. For example, glass, quartz, plastic, or the like can be used for the substrate 100. A flexible substrate may be used. The flexible substrate is a substrate that can be bent, such as a plastic substrate made of, for example, polycarbonate, polyarylate, or polyether sulfone. Alternatively, a film (made of polypropylene, polyester, polyvinyl fluoride, polyvinyl chloride, or the like), a film on which an inorganic substance is deposited, or the like can be used. Note that another substrate can be used as long as it can function as a support in a process of manufacturing the light-emitting element.

For the first electrode 101 and the second electrode 103, a metal, an alloy, an electrically conductive compound, a mixture thereof, and the like can be used. Specifically, indium oxide-tin oxide (ITO: indium tin oxide), indium oxide-tin oxide containing silicon or silicon oxide, indium oxide-zinc oxide, indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as magnesium (Mg), calcium (Ca), or strontium (Sr), an alloy containing such an element (e.g., MgAg or AlLi), a rare earth metal such as europium (Eu) or ytterbium (Yb), an alloy containing such an element, graphene, and the like can be used. The first electrode 101 and the second electrode 103 can be formed by, for example, a sputtering method, an evaporation method (including a vacuum evaporation method), or the like.

As a substance having a high hole-transport property that is used for the hole-injection layer 111, the hole-transport layer 112, and the charge-generation layer 116, a π-electron rich heteroaromatic compound (e.g., a carbazole derivative or an indole derivative) or an aromatic amine compound is preferable; for example, the following substances can be used: a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1, 1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4',4''-(benzene-1,3,5-triyl)tri(dibenzofuran) (abbreviation: DBF3P-II), or 4-{3-[3-(9-phenyl-9H-fluoren-9-yl)phenyl]phenyl}dibenzofuran (abbreviation: mmDBFFLBi-II). In the above-mentioned substances, a compound having an aromatic amine skeleton or a compound having a carbazole skeleton is preferable because of its high reliability and its high hole-transport property, which contributes to a reduction in driving voltage.

Furthermore, as a material that can be used for the hole-injection layer 111, the hole-transport layer 112, and the charge-generation layer 116, a high molecular compound such as poly(N-vinylcarbazole) (abbreviation: PVK), poly (4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

As each of the hole-injection layer 111, the hole-transport layer 112, and the charge-generation layer 116, a layer in which any of the substances having a high hole-transport property given above and a substance having an acceptor property are mixed is preferably used, in which case a favorable carrier-injection property is obtained. Examples of the acceptor substance to be used include a transition metal oxide and an oxide of a metal belonging to any of Groups 4 to 8 of the periodic table. Specifically, molybdenum oxide is particularly preferable.

Furthermore, for the hole-injection layer 111, the hole-transport layer 112, and the charge-generation layer 116, an organic compound of one embodiment of the present invention, which is described later, can be used.

The light-emitting layer 113 is preferably a layer which includes, for example, an electron-transport material as a host material, a hole-transport material as an assist material, and a light-emitting material, which converts triplet-excitation energy into light emission, as a guest material.

As the electron-transport material, a π-electron deficient heteroaromatic compound such as a nitrogen-containing heteroaromatic compound is preferable; for example, the following can be given: heterocyclic compounds (e.g., an oxadiazole derivative, an imidazole derivative, and a triazole derivative) having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds (e.g., a pyrazine derivative, a pyrimidine derivative, a pyridazine derivative, a quinoxaline derivative, and a dibenzoquinoxaline derivative) having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6-mPnP2Pm), and 4,6-bis[3-(4-dibenzothienyl)phenyl]pyrimidine (abbreviation: 4,6mDBTP2Pm-II); and heterocyclic compounds (e.g., a pyridine derivative, a quinoline derivative, and a dibenzoquinoline derivative) having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the materials given above, the heterocyclic compound having a diazine skeleton and the heterocyclic compound having a pyridine skeleton have high reliability and are thus preferable. Specifically, the heterocyclic compound having a diazine (pyrimidine or pyrazine) skeleton has a high electron-transport property to contribute to a reduction in driving voltage.

As the hole-transport material, a substance having a high hole-transport property, which can be used for the hole-injection layer 111, the hole-transport layer 112, and the charge-generation layer 116, can be used. Alternatively, an organic compound of one embodiment of the present invention, which is described later, can be used.

Note that it is preferable that the electron-transport material and the hole-transport material do not have an absorption spectrum in the blue wavelength range. Specifically, absorption edge of the absorption spectrum is preferably less than or equal to 440 nm.

On the other hand, examples of a light-emitting material which converts triplet-excitation energy into light emission include a phosphorescent material and a thermally activated delayed fluorescence (TADF) material.

As the phosphorescent material, for example, a phosphorescent material having an emission peak at 440 nm to 520 nm is given, examples of which include organometallic iridium complexes having 4H-triazole skeletons, such as tris{2-[5-(2-methylphenyl)-4-(2,6-dimethylphenyl)-4H-1,2,4-triazol-3-yl-κN2]phenyl-κC}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$, and tris[4-(3-biphenyl)-5-isopropyl-3-phenyl-4H-1,2,4-triazolato]iridium (III) (abbreviation: Ir(iPrptz-3b)$_3$); organometallic iridium complexes having 1H-triazole skeletons, such as tris[3- methyl-1-(2-methylphenyl)-5-phenyl-1H-1,2,4-triazolato]iridium(III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having imidazole skeletons, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), and bis[2-(4',6'-difluorophenyl)pyridinato-N,C$^{2'}$]iridium(III) acetylacetonate (abbreviation: FIr(acac)). Among the materials given above, the organometallic iridium complex having a 4H-triazole skeleton has high reliability and high emission efficiency and is thus especially preferable.

Examples of the phosphorescent material having an emission peak at 520 nm to 600 nm include organometallic iridium complexes having pyrimidine skeletons, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[4-(2-norbornyl)-6-phenylpyrimidinato]iridium(III) (endo- and exo-mixture) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), and (acetylacetonato)bis(4,6-diphenylpyrimidinato)iridium(III) (abbreviation: Ir(dppm)$_2$(acac)); organometallic iridium complexes having pyrazine skeletons, such as (acetylacetonato)bis(3,5-dimethyl-2-phenylpyrazinato)iridium(III) (abbreviation: Ir(mppr-Me)$_2$(acac)) and (acetylacetonato)bis(5-isopropyl-3-methyl-2-phenylpyrazinato)iridium(III) (abbreviation: Ir(mppr-iPr)$_2$(acac)); organometallic iridium complexes having pyridine skeletons, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$acac), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(III) (abbreviation: Ir(pq)$_3$, and bis(2-phenylquinolinato-N,C$^{2'}$)iridium(acetylacetonate) (abbreviation: Ir(pq)$_2$(acac)); and a rare earth metal complex such as tris(acetylacetonato) (monophenanthroline)terbium(III) (abbreviation: Tb(acac)$_3$(Phen)). Among the materials given above, the organometallic iridium complex having a pyrimidine skeleton has distinctively high reliability and emission efficiency and is thus especially preferable.

Examples of the phosphorescent material having an emission peak at 600 nm to 700 nm include organometallic iridium complexes having pyrimidine skeletons, such as bis[4,6-bis(3-methylphenyl)pyrimidinato](diisobutylylmethano)iridium(III) (abbreviation: Ir(5mdppm)$_2$(dibm)), bis[4,6-bis(3-methylphenyl)pyrimidinato](dipivaloylmethanato)iridium(III) (abbreviation: Ir(5mdppm)$_2$(dpm)), and bis[4,6-di(naphthalen-1-yl)pyrimidinato](dipivaloylmethanato)iridium(III) (abbreviation: Ir(d1npm)$_2$(dpm)); organometallic iridium complexes having pyrazine skeletons, such as (acetylacetonato)bis(2,3,5-triphenylpyrazinato)iridium (III) (abbreviation: Ir(tppr)$_2$(acac)), bis(2,3,5-triphenylpyrazinato) (dipivaloylmethanato)iridium(III) (abbreviation: Ir(tppr)$_2$(dpm)), or (acetylacetonato)bis[2,3-bis(4-fluorophenyl)quinoxalinato]iridium(III) (abbreviation: Ir(Fdpq)$_2$(acac)); organometallic iridium complexes having pyridine skeletons, such as tris(1-phenylisoquinolinato-N,C$^{2'}$)iridium(III) (abbreviation: Ir(piq)$_3$) and bis(1-phenylisoquinolinato-N,C$^{2'}$)iridium(III) acetylacetonate (abbreviation: Ir(piq)$_2$acac); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: Eu(DBM)$_3$(Phen)) and tris[1-(2-thenoyl)-3,3,3-trifluoroacetonato](monophenanthroline)europium(III) (abbreviation: Eu(TTA)$_3$(Phen)). Among the materials given above, the organometallic complex having a pyrimidine skeleton has distinctively high reliability and emission efficiency and is thus especially preferable. Further, the organometallic iridium complex having a pyrazine skeleton can provide red light emission with favorable chromaticity.

It is preferable that at least one of the hole-transport layer 112 and the light-emitting layer 113 include an organic compound having a skeleton represented by General Formula (G0). Note that the organic compound having the skeleton represented by General Formula (G0) is one embodiment of the present invention. The organic compound of one embodiment of the present invention is a material having an excellent hole-transport property.

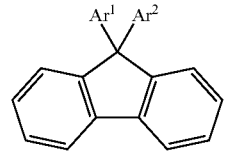

(G0)

In General Formula (G0), Ar$^1$ and Ar$^2$ are each independently any one of a phenyl group, a biphenyl group, and a group in which 3 to 6 benzene rings are bonded at the meta-positions; Ar$^1$ has a substituent and the substituent has a carbazole skeleton; and Ar$^2$ is unsubstituted. With Ar$^1$ having the above structure, a hole-transport material having high triplet-excitation energy level and high heat resistance can be obtained. Furthermore, with Ar$^2$ that is unsubstituted, the reliability of the element can be enhanced.

Note that as the organic compound having the skeleton represented by General Formula (G0), specifically, the structure of General Formula (G1) is more preferable. An organic compound represented by General Formula (G1) is one embodiment of the present invention.

(G1)

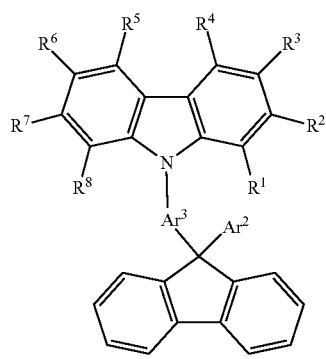

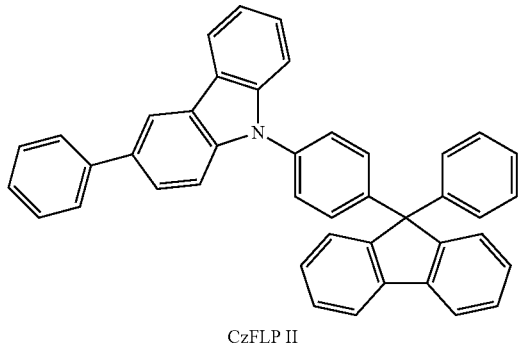

CzFLP II

In General Formula (G1), $Ar^2$ and $Ar^3$ are each independently any one of a phenyl group, a biphenyl group, and a group in which 3 to 6 benzene rings are bonded at the meta-positions; and $Ar^2$ is unsubstituted. In addition, $R^1$ to $R^8$ are each independently any one of hydrogen, an alkyl group having 1 to 12 carbon atoms, a substituted or unsubstituted phenyl group, and a substituted or unsubstituted biphenyl group.

In General Formula (G1), it is more preferale in view of triplet-excitation energy level that $Ar^2$ be a phenyl group or a biphenyl group and $Ar^3$ be a phenylene group or a biphenyldiyl group. It is still more preferable that $Ar^3$ be a metaphenylene group or a biphenyl-3,3'-diyl group. Such structures are advantageous in view of triplet-excitation energy level, and furthermore, a molecule has a bulky skeleton and stable film quality can be obtained, leading to a long lifetime of an element.

Specifically, organic compounds represented by General Formulae (G2-1), (G2-2), and (G3) are preferable as the organic compound having a skeleton represented by General Formula (G0) and the organic compound represented by General Formula (G1). Note that each of the organic compounds represented by Structural Formulae (G2-1), (G2-2), and (G3) is one embodiment of the present invention.

(G3)

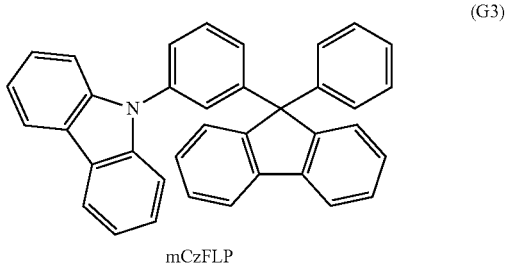

mCzFLP

Specific examples of $Ar^1$ in General Formula (G0) include substituents represented by Structural Formulae (Ar-1) to (Ar-11).

(Ar-1)

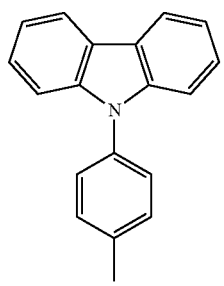

(G2-1)

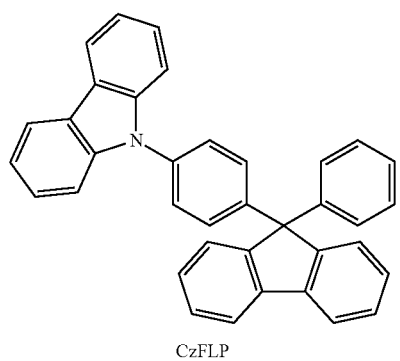

CzFLP (Ar-2)

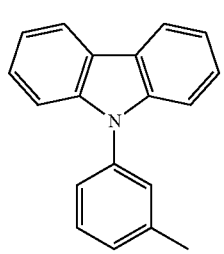

-continued
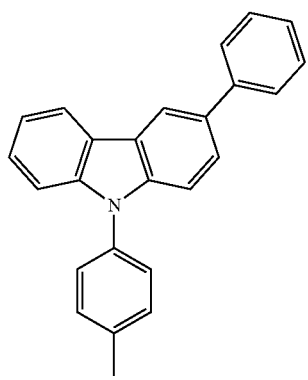
(Ar-3)
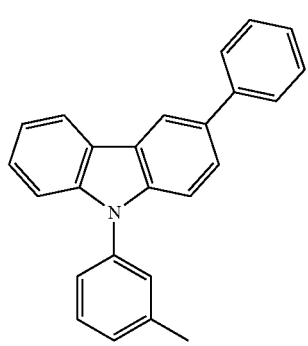
(Ar-4)
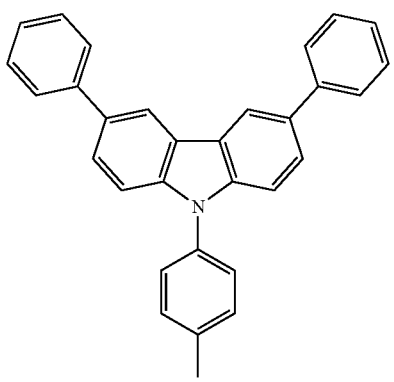
(Ar-5)
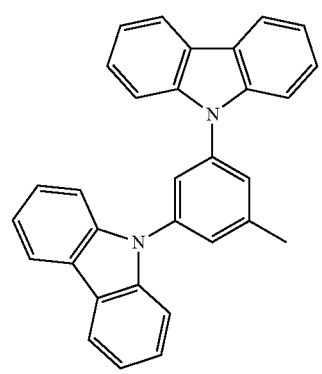
(Ar-6)
-continued
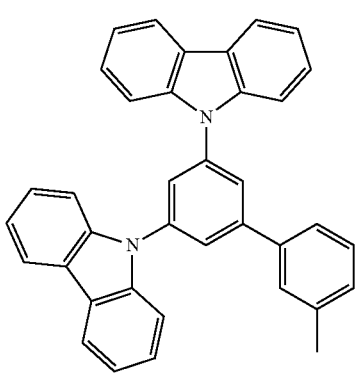
(Ar-7)
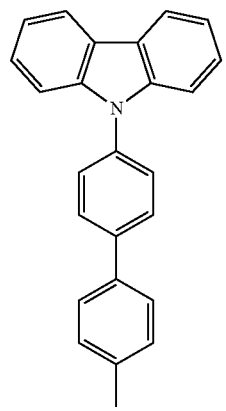
(Ar-8)
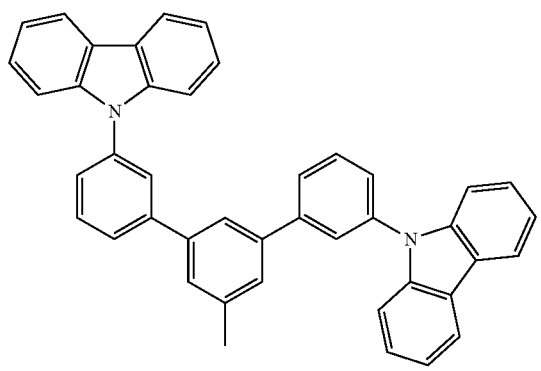
(Ar-9)
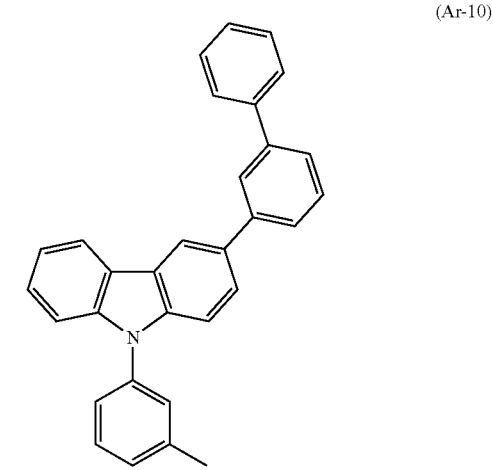
(Ar-10)

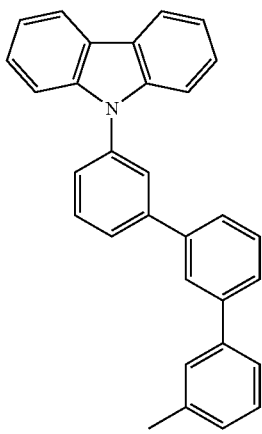
(Ar-11)

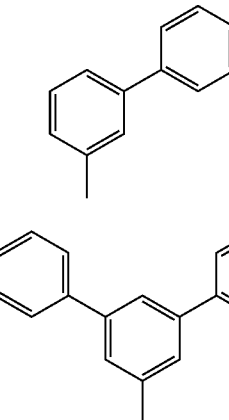
(Ar-23)

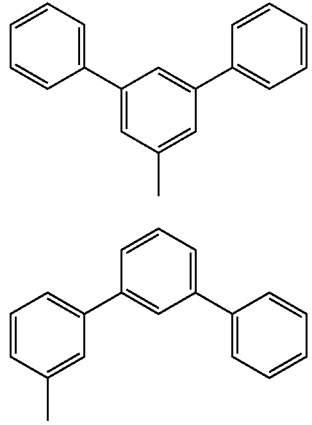
(Ar-24)

As shown by Structural Formulae (Ar-1) to (Ar-11), one or more carbazolyl groups are bonded to any of a phenyl group, a biphenyl group, and a group in which 3 to 6 benzene rings are bonded at the meta-positions as a substituent. In the case where the number of carbazolyl groups is one (e.g., Structural Formulae (Ar-1) and (Ar-2)), the T1 level can be kept high, which is preferable. In the case where the number of carbazolyl groups is two or more (e.g., Structural Formulae (Ar-6), (Ar-7), and (Ar-9)), the structure becomes more steric and the thermophysical property is improved, which is preferable. In the case where an aryl group such as a phenyl group is bonded to the 3-position of such a carbazolyl group (e.g., Structural Formulae (Ar-3), (Ar-4), (Ar-5), and (Ar-10)), the carrier-transport property is improved, which is preferable. In addition, the thermophysical property is also improved, which is preferable. In the case where the carbazolyl groups are bonded at the meta-positions with respect to the benzene skeleton (e.g., Structural Formulae (Ar-2), (Ar-4), (Ar-6), (Ar-7), (Ar-9), (Ar-10), and (Ar-11)), the amorphous property is increased, which is preferable.

Specific examples of $Ar^3$ in General Formula (G1) include substituents represented by Structural Formulae (Ar-21) to (Ar-28).

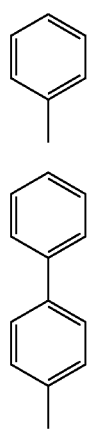
(Ar-21)

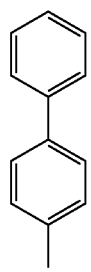
(Ar-22)

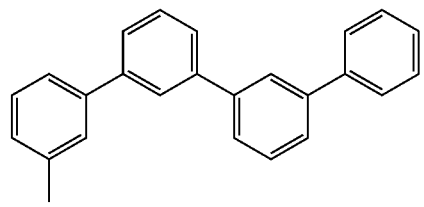
(Ar-25)

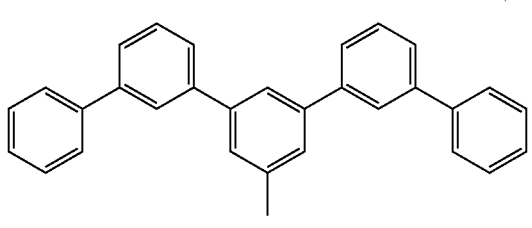
(Ar-26)

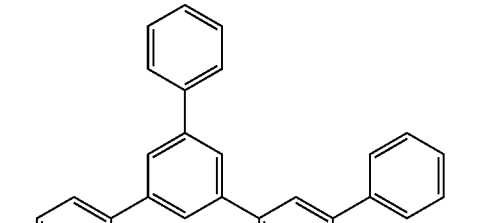
(Ar-27)

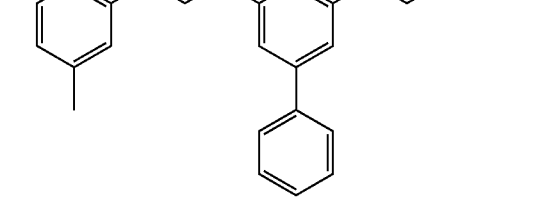
(Ar-28)

At this time, the number of benzene rings is preferably large because the thermophysical property can be improved. In the case where plural benzene rings are bonded, the benzene rings are preferably bonded at the meta-positions (e.g., Structural Formulae (Ar-23) to (Ar-28)) because the amorphous property can be improved and the T1 level is less likely to decrease.

Specific examples of $R^1$ to $R^8$ in General Formula (G1) include substituents represented by Structural Formulae (R-1) to (R-8).

Specific examples of the organic compounds represented by General Formulae (G0) and (G1) include organic compounds represented by Structural Formulae (100) to (118).

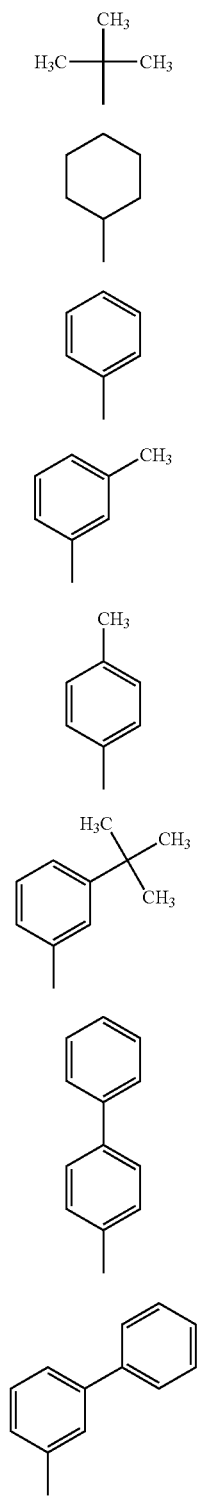

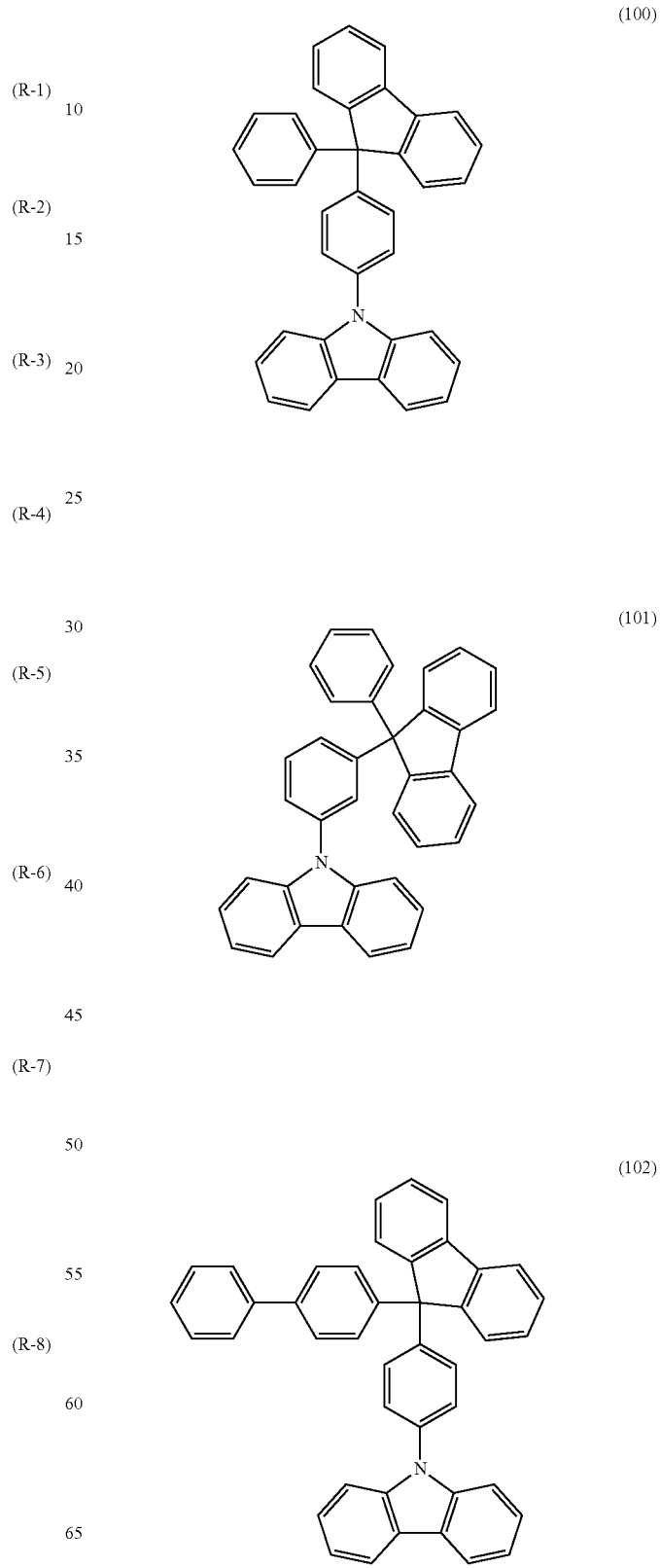

(103)
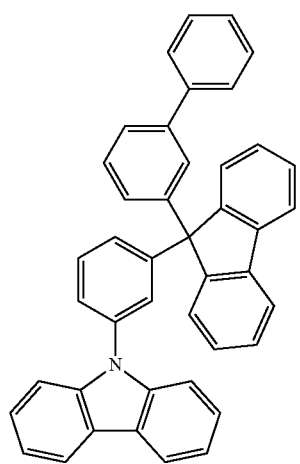
(104)
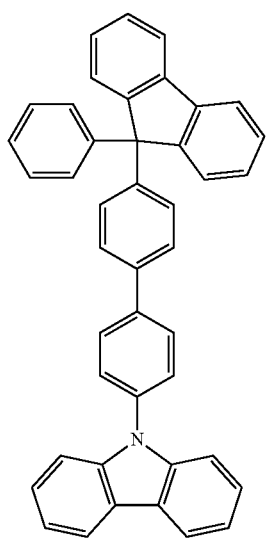
(105)
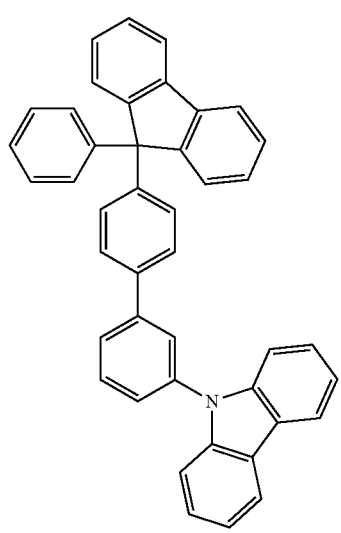
(106)
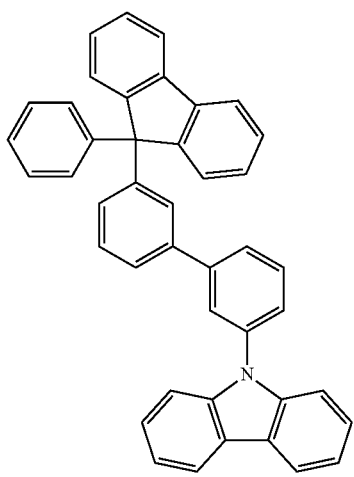
(107)
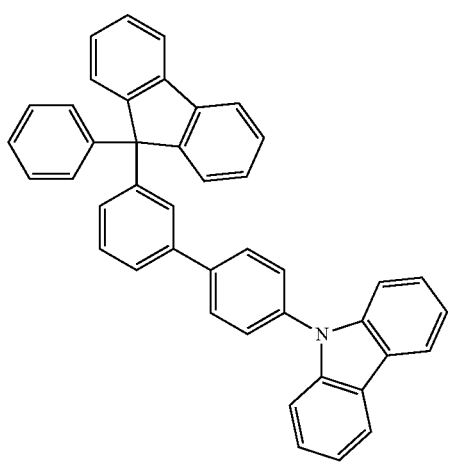
(108)
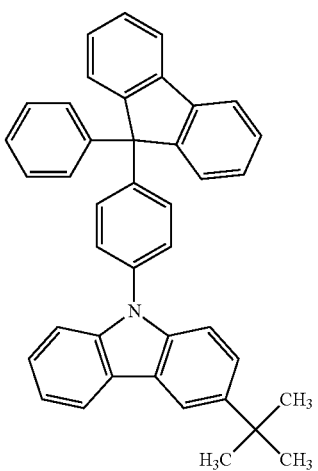

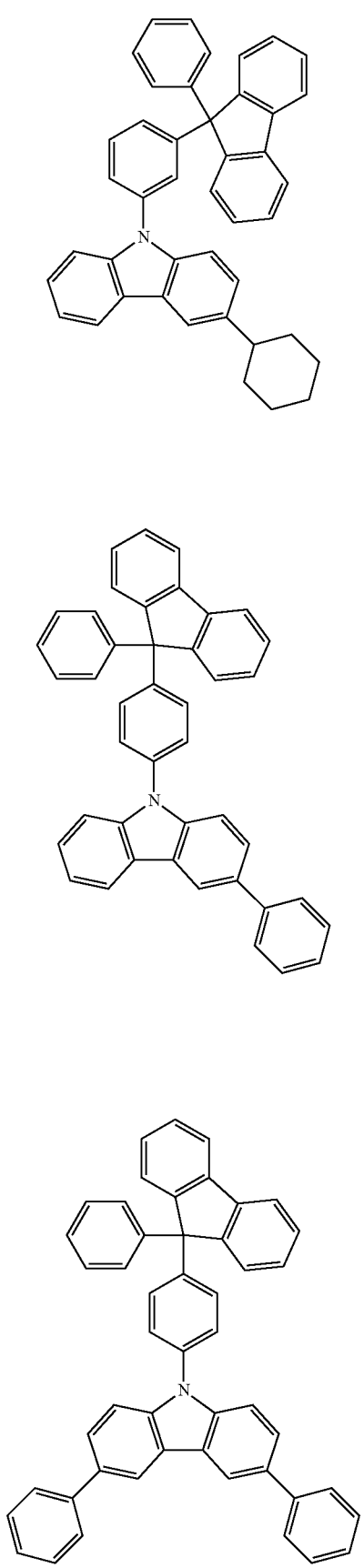
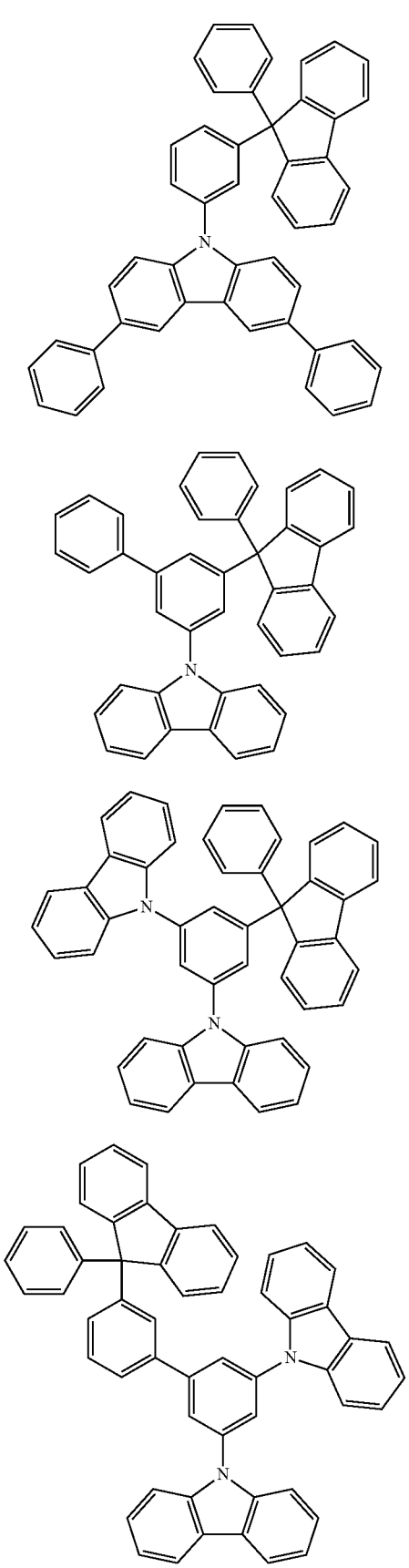

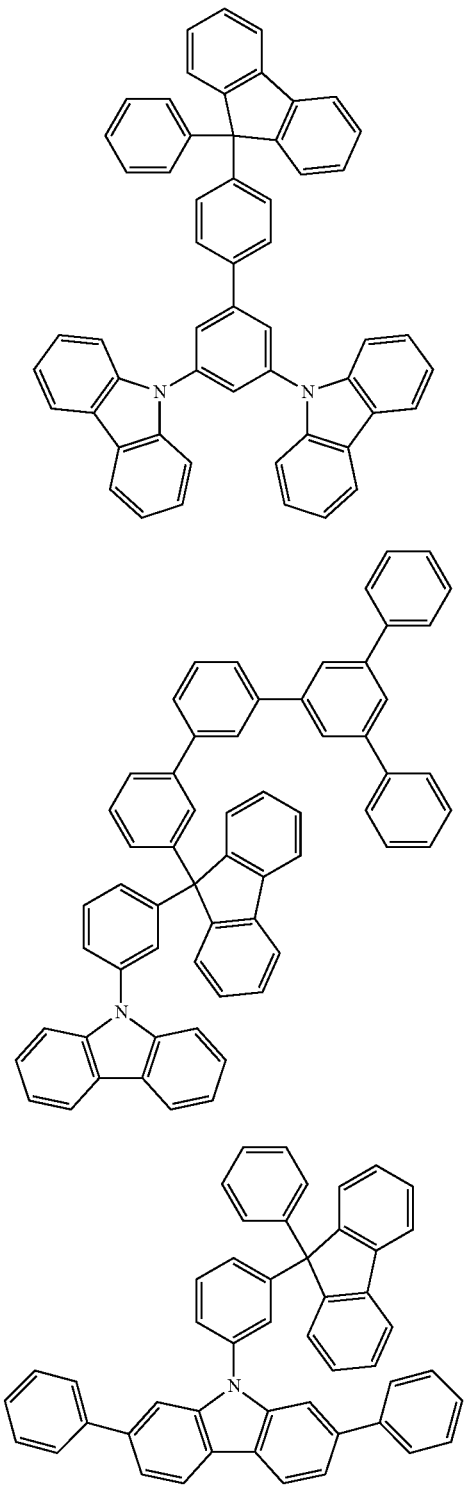

(116)

(117)

(118)

A variety of reactions can be applied to a synthesis method of the organic compound of one embodiment of the present invention. For example, synthesis reactions described below enable the synthesis of the organic compound represented by General Formula (G1). Note that the synthesis method of the organic compound is not limited to the synthesis method below.

<Synthesis Method of Organic Compound Represented by General Formula (G1)>

As shown in Synthesis Scheme (A-1), the fluorene compound represented by General Formula (G1) can be obtained by coupling a halide fluorene compound (a1) and a carbazole compound (a2).

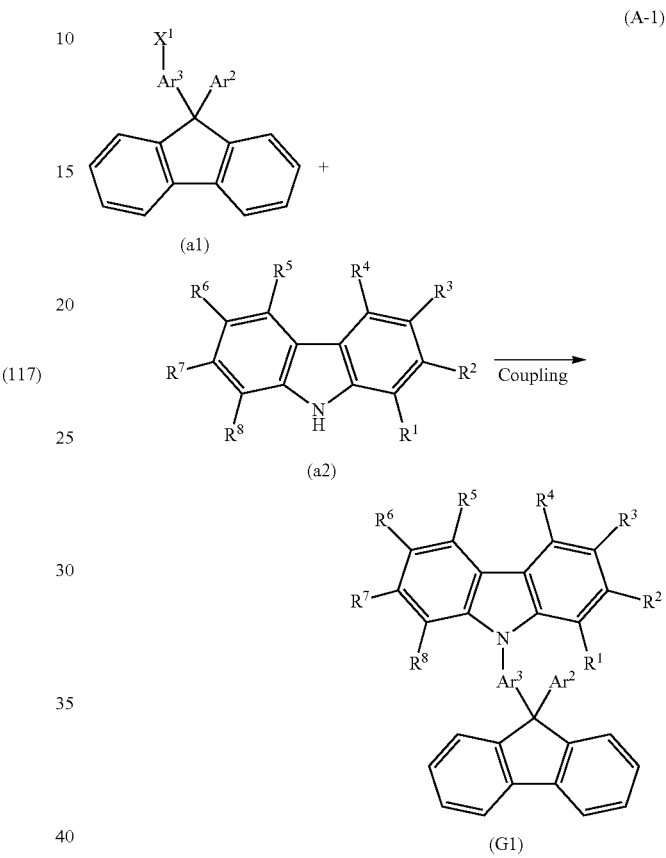

(A-1)

(a1)

(a2)

(G1)

In Synthesis Scheme (A-1), $Ar^2$ and $Ar^3$ are each independently any one of a phenyl group, a biphenyl group, and a group in which 3 to 6 benzene rings are bonded at the meta-positions; and $Ar^2$ is unsubstituted. In addition, $R^1$ to $R^8$ are each independently any one of hydrogen, an alkyl group having 1 to 12 carbon atoms, a substituted or unsubstituted phenyl group, and a substituted or unsubstituted biphenyl group. Furthermore, $X^1$ is a halogen group; chlorine is preferred, bromine is more preferred, and iodine is still more preferred in terms of reactivity.

In Synthesis Scheme (A-1), a variety of reaction conditions can be employed for the coupling reaction between an aryl compound having a halogen group and the 9-position of the carbazole. As an example of the reaction conditions, a synthesis method using a metal catalyst in the presence of a base can be employed.

Specifically, the Buchwald-Hartwig reaction or the Ullmann reaction can be used.

Thus, the organic compound of one embodiment of the present invention can be synthesized.

Note that the organic compound is a material having a high hole-transport property, and can be used as an assist material in the light-emitting layer 113. The light-emitting layer 113 includes the organic compound (an assist material), the material (a host material) having a high electron-transport property, and the light-emitting material (a guest material) which converts triplet-excitation energy into light emission, whereby phosphorescence with high emission efficiency can be obtained.

Further, the organic compound of one embodiment of the present invention has a high $T_1$ level and thus also has a high singlet excited energy level ($S_1$ level). Thus, the organic compound of one embodiment of the present invention can also be used as an assist material for a fluorescent light-emitting material in the visible light region.

The electron-transport layer 114 is a layer containing a substance having a high electron-transport property. For the electron-transport layer 114, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$) can be used in addition to the above-described electron-transport materials. Further, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further, a high molecular compound such as poly(2,5-pyridine-diyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used. The substances given here are mainly ones having an electron mobility of $10^{-6}$ cm$^2$/Vs or higher. Note that any other substance may be used for the electron-transport layer 114 as long as the substance has an electron-transport property higher than a hole-transport property.

The electron-transport layer 114 is not limited to a single layer, and may be a stack of two or more layers containing any of the above substances.

The electron-injection layer 115 is a layer containing a substance having a high electron-injection property. For the electron-injection layer 115, an alkali metal compound or an alkaline earth metal compound, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. Any of the substances for forming the electron-transport layer 114, which are given above, can also be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex and a heteroaromatic compound), which are given above, can be used. As the electron donor, a substance exhibiting an electron-donating property to the organic compound may be used. Specifically, an alkali metal, an alkaline-earth metal, and a rare earth metal are preferable, and lithium, cesium, magnesium, calcium, erbium, and ytterbium are given. Further, an alkali metal oxide or an alkaline-earth metal oxide is preferable; examples thereof include lithium oxide, calcium oxide, and barium oxide. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, electron-injection layer 115, and charge-generation layer 116 can be formed by a method such as an evaporation method (e.g., a vacuum evaporation method), an ink jet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through the first electrode 101, the second electrode 103, or both. Thus, the first electrode 101, the second electrode 103, or both are electrodes having a light-transmitting property.

Note that the structure described in this embodiment can be combined as appropriate with any of the structures described in the other embodiments.

(Embodiment 2)

In this embodiment, a light-emitting element in which the organic compound of one embodiment of the present invention, the light-emitting material which converts triplet-excitation energy into light emission, and the electron-transport material are used for a light-emitting layer will be described with reference to FIGS. 2A and 2B.

Figure 2A:
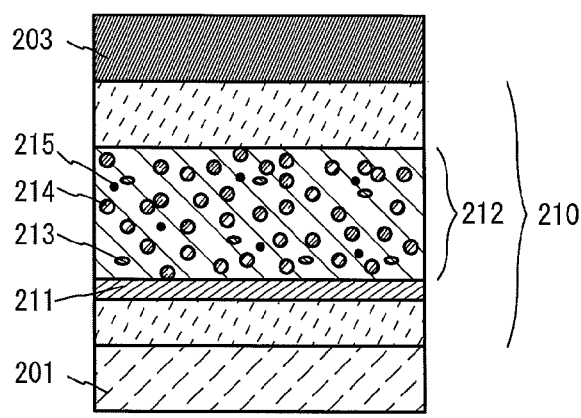
FIGS. 2A and 2B illustrate a light-emitting element of one embodiment of the present invention.
Figure 2B:
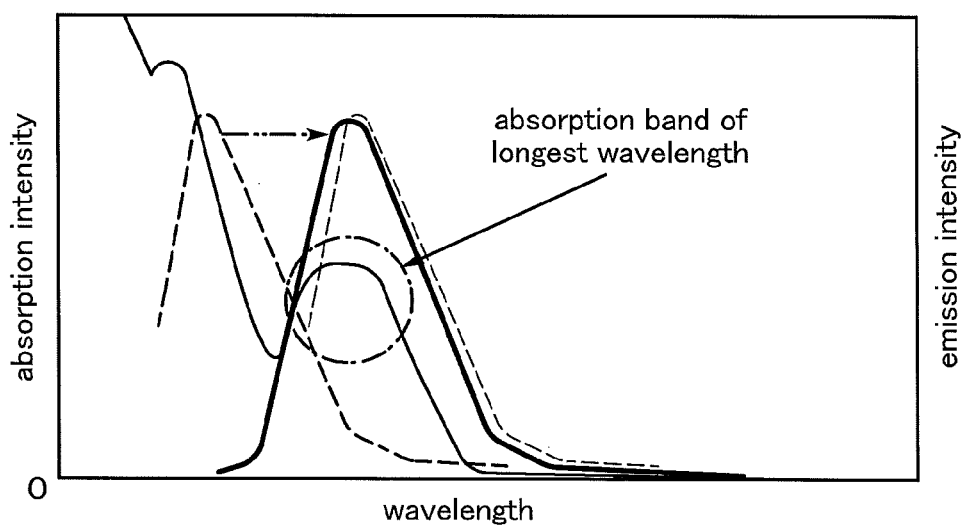

A light-emitting element described in this embodiment includes an EL layer 210 between a pair of electrodes (a first electrode 201 and a second electrode 203) as illustrated in FIG. 2A. Note that the EL layer 210 includes at least a hole-transport layer 211 and a light-emitting layer 212 and may further include a hole-injection layer, an electron-transport layer, an electron-injection layer, a charge-generation layer, and the like. The substances given in Embodiment 1 can be used for the hole-injection layer, the electron-transport layer, the electron-injection layer, and the charge-generation layer. Furthermore, the first electrode 201 is used as an anode and the second electrode 203 is used as a cathode in this embodiment.

The organic compound of one embodiment of the present invention is included in at least one of the hole-transport layer 211 and the light-emitting layer 212 described in this embodiment.

The light-emitting layer 212 includes a first organic compound 213, a second organic compound 214, and a third organic compound 215. In this embodiment, the first organic compound 213, the second organic compound 214, and the third organic compound 215 are used as a host material, an assist material, and a guest material, respectively. The organic compound of one embodiment of the present invention is a substance having a high hole-transport property, and can be applied to the second organic compound 214 that is used as an assist material.

When the light-emitting layer 212 has the structure in which the guest material is dispersed in the host material, the crystallization of the light-emitting layer can be suppressed. Further, it is possible to suppress concentration quenching due to high concentration of the guest material; thus, the light-emitting element can have higher emission efficiency.

Note that it is preferable that a triplet excited energy level ($T_1$ level) of each of the first organic compound 213 (a host material) and the second organic compound 214 (an assist material) be higher than that of the third organic compound 215 (a guest material). This is because, when the $T_1$ level of the first organic compound 213 (or the second organic compound 214) is lower than that of the third organic compound 215, the triplet excited energy of the third organic compound 215, which is to contribute to light emission, is quenched by the first organic compound 213 (or the second organic compound 214) and accordingly the emission efficiency decreases.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) largely overlap with an absorption spectrum of a guest material (specifically, spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, because the phosphorescence spectrum of the host material is located on the longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For this reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound 213 and the second organic compound 214 preferably forms an excited complex (also referred to as exciplex). Thus, in the light-emitting layer 212, a fluorescence spectrum of the first organic compound 213 and that of the second organic compound 214 are converted into an emission spectrum of the exciplex which is located on a longer wavelength side. Moreover, when the first organic compound 213 and the second organic compound 214 are selected in such a manner that the emission spectrum of the exciplex largely overlaps with the absorption spectrum of the guest material (the third organic compound 215), energy transfer from a singlet excited state can be maximized (see FIG. 2B).

Note that also in the case of a triplet excited state, energy transfer from the exciplex, not the host material, is considered to occur.

The electron-transport material described in Embodiment 1 is preferably used as the first organic compound 213. The hole-transport material described in Embodiment 1 or the organic compound of one embodiment of the present invention is preferably used as the second organic compound 214.

The phosphorescent material described in Embodiment 1 is preferably used as the third organic compound 215.

The above-described combination of the first organic compound 213 and the second organic compound 214 is an example of the combination which enables an exciplex to be formed. The combination is determined so that the emission spectrum of the exciplex overlaps with the absorption spectrum of the third organic compound 215 and that the peak of the emission spectrum of the exciplex has a longer wavelength than the peak of the absorption spectrum of the third organic compound 215.

Note that the electron-transport material and the hole-transport material form the first organic compound 213 and the second organic compound 214; adjusting the mixture ratio thereof can control the carrier balance. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of a light-emitting element.

Note that although the light-emitting element described in this embodiment is one structural example of a light-emitting element, a light-emitting element having another structure which is described in another embodiment can also be applied to a light-emitting device of one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed using only either an n-type TFT or a p-type TFT or both. Furthermore, there is no particular limitation on the crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 3)

In this embodiment, as one embodiment of the present invention, a light-emitting element (hereinafter referred to as tandem light-emitting element) in which a charge generation layer is provided between a plurality of light-emitting layers will be described.

Figure 3A:
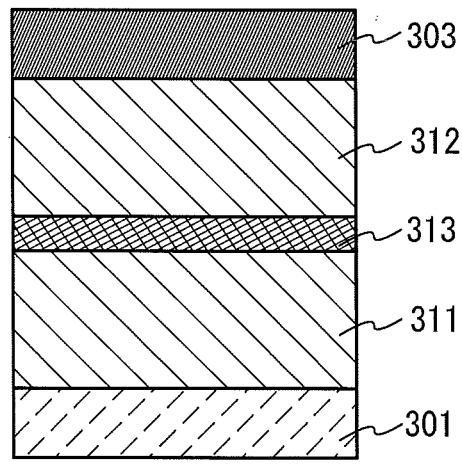
FIGS. 3A and 3B each illustrate a light-emitting element of one embodiment of the present invention.

A light-emitting element described in this embodiment is a tandem light-emitting element including a plurality of light-emitting layers (a first light-emitting layer 311 and a second light-emitting layer 312) between a pair of electrodes (a first electrode 301 and a second electrode 303), as illustrated in FIG. 3A.

In this embodiment, the first electrode 301 functions as an anode, and the second electrode 303 functions as a cathode. Note that the first electrode 301 and the second electrode 303 can have structures similar to those described in Embodiment 2. In addition, although the plurality of light-emitting layers (the first light-emitting layer 311 and the second light-emitting layer 312) may have structures similar to those described in Embodiment 1 or 2, any of the light-emitting layers may have a structure similar to that described in Embodiment 1 or 2. In other words, the structures of the first light-emitting layer 311 and the second light-emitting layer 312 may be the same or different from each other and can be similar to those described in Embodiment 1 or 2.

In the first light-emitting layer 311, the second light-emitting layer 312, or both, a hole-transport layer (not illustrated) is provided on the first electrode 301 side.

Further, a charge-generation layer 313 is provided between the plurality of light-emitting layers (the first light-emitting layer 311 and the second light-emitting layer 312). The charge generation layer 313 has a function of injecting electrons into one of the light-emitting layers and injecting holes into the other of the light-emitting layers when voltage is applied to the first electrode 301 and the second electrode 303. In this embodiment, when voltage is applied such that the potential of the first electrode 301 is higher than that of the second electrode 303, the charge-generation layer 313 injects electrons into the first light-emitting layer 311 and injects holes into the second light-emitting layer 312.

Note that in terms of light extraction efficiency, the charge-generation layer 313 preferably has a light-transmitting property with respect to visible light (specifically, the charge-generation layer 313 has a visible light transmittance of 40% or more). Further, the charge-generation layer 313 functions even if it has lower conductivity than the first electrode 301 or the second electrode 303.

The charge-generation layer 313 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances given here are mainly ones having a hole mobility of $10^{-6}$ cm$^2$/Vs or higher. Note that any other substance may be used as long as the substance has a hole-transport property higher than an electron-transport property.

Further, as the electron acceptor, 7,7,8,8-tetracyano-2,3,5,6-tetrafluoro quino dimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these metal oxides, molybdenum oxide is especially preferable since it is stable in the air, has a low hygroscopic property, and is easily handled.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Other than metal complexes, PBD, OXD-7, TAZ, BPhen, BCP, or the like can be used. The substances given here are mainly ones having an electron mobility of $10^{-6}$ cm$^2$/Vs or higher. Note that any other substance may be used as long as the substance has an electron-transport property higher than a hole-transport property.

As the electron donor, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may also be used as the electron donor.

Note that forming the charge-generation layer 313 by using any of the above materials can suppress an increase in driving voltage caused by the stack of the light-emitting layers.

Figure 3B:
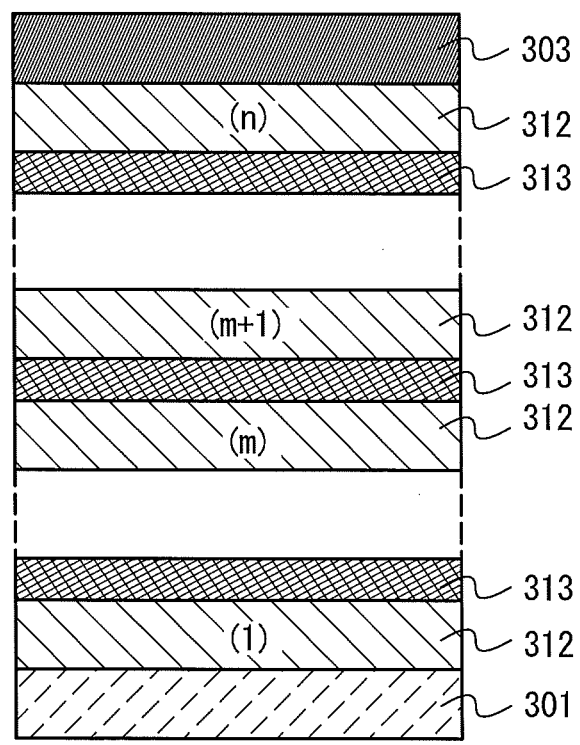

Although the light-emitting element having two light-emitting layers is illustrated in FIG. 3A, the present invention can be similarly applied to a light-emitting element in which n light-emitting layers (n is three or more) are stacked as illustrated in FIG. 3B. In the case where a plurality of light-emitting layers are provided between a pair of electrodes as in the light-emitting element of this embodiment, by providing a charge-generation layer 313 between the light-emitting layers, the light-emitting element can emit light in a high luminance region while the current density is kept low. Since the current density can be kept low, the element can have a long lifetime. When the light-emitting element is applied to lighting, voltage drop due to resistance of an electrode material can be reduced, thereby achieving homogeneous light emission in a large area. Moreover, a light-emitting device which can be driven at low voltage and has low power consumption can be achieved.

By making the light-emitting layers emit light of different colors from each other, the light-emitting element can provide light emission of a desired color as a whole. For example, by forming a light-emitting element having two light-emitting layers such that the emission color of the first light-emitting layer and the emission color of the second light-emitting layer are complementary colors, the light-emitting element can provide white light emission as a whole. Note that "complementary colors" refer to colors which produce an achromatic color when mixed. In other words, when lights obtained from substances which emit light of complementary colors are mixed, white emission can be obtained.

Further, the same can be applied to a light-emitting element having three light-emitting layers. For example, the light-emitting element as a whole can provide white light emission when the emission color of the first light-emitting layer is red, the emission color of the second light-emitting layer is green, and the emission color of the third light-emitting layer is blue.

Note that the structure described in this embodiment can be combined as appropriate with any of the structures described in the other embodiments.

(Embodiment 4)

In this embodiment, a light-emitting device of one embodiment of the present invention will be described.

A light-emitting device described in this embodiment has a micro optical resonator (microcavity) structure in which a light resonant effect between a pair of electrodes is utilized.

Figure 4:
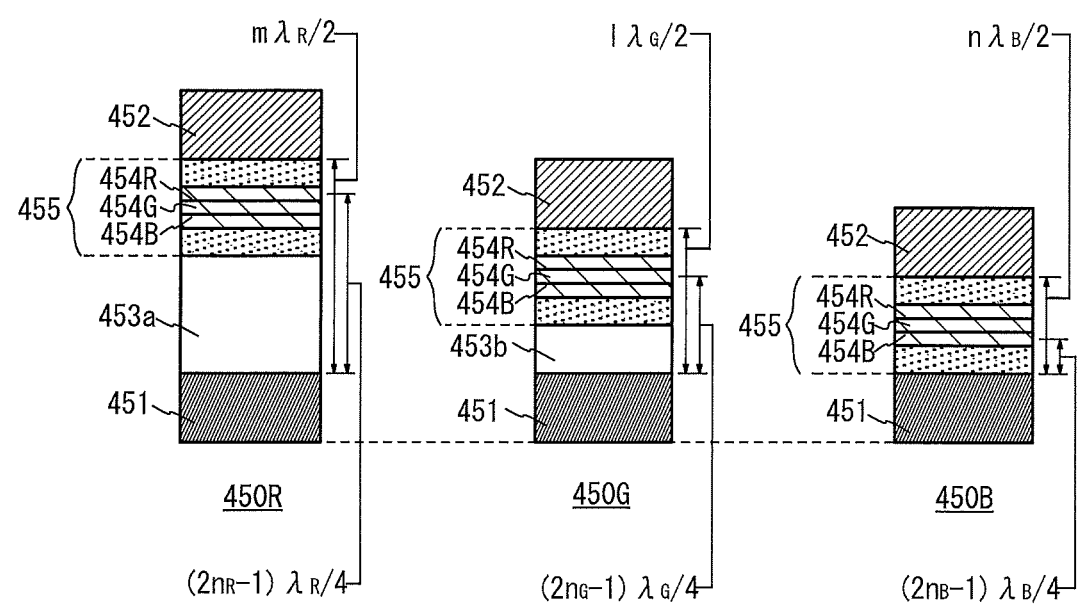
FIG. 4 illustrates a light-emitting element of one embodiment of the present invention.

The light-emitting device includes a plurality of light-emitting elements each of which includes at least an EL layer 455 between a pair of electrodes (a reflective electrode 451 and a semi-transmissive and semi-reflective electrode 452) as illustrated in FIG. 4. Further, the EL layer 455 includes at least a hole-transport layer (not illustrated) and light-emitting layers (a first light-emitting layer 454B, a second light-emitting layer 454G, and a third light-emitting layer 454R). The EL layer 455 may further include a hole-injection layer, an electron-transport layer, an electron-injection layer, a charge generation layer, and the like.

A first light-emitting element 450R has a structure in which a first transparent conductive layer 453a, the EL layer 455 including the first light-emitting layer 454B, the second light-emitting layer 454G, and the third light-emitting layer 454R as its part, the semi-transmissive and semi-reflective electrode 452 are sequentially stacked over the reflective electrode 451. A second light-emitting element 450G has a structure in which a second transparent conductive layer 453b, the EL layer 455, and the semi-transmissive and semi-reflective electrode 452 are sequentially stacked over the reflective electrode 451. A third light-emitting element 450B has a structure in which the EL layer 455 and the semi-transmissive and semi-reflective electrode 452 are sequentially stacked over the reflective electrode 451.

Note that the reflective electrode 451, the EL layer 455, and the semi-transmissive and semi-reflective electrode 452 are common to the light-emitting elements (the first light-emitting element 450R, the second light-emitting element 450G, and the third light-emitting element 450B). The first light-emitting layer 454B emits light ($\lambda_B$) having a peak in a wavelength region from 420 nm to 480 nm, the second light-emitting layer 454G emits light ($\lambda_G$) having a peak in a wavelength region from 500 nm to 550 nm, and the third light-emitting layer 454R emits light ($\lambda_R$) having a peak in a wavelength region from 600 nm to 760 nm. Thus, in each of the light-emitting elements (the first light-emitting element 450R, the second light-emitting element 450G, and the third light-emitting element 450B), the lights emitted from the first light-emitting layer 454B, the second light-emitting layer 454G, and the third light-emitting layer 454R overlap with each other; accordingly, light having a broad emission spectrum that covers a visible light range can be emitted. Note that the above wavelengths satisfy the relation of $\lambda_B<\lambda_G<\lambda_R$.

Each of the light-emitting elements described in this embodiment has a structure in which the EL layer 455 is interposed between the reflective electrode 451 and the semi-transmissive and semi-reflective electrode 452. The lights emitted in all directions from the light-emitting layers included in the EL layer 455 are resonated by the reflective electrode 451 and the semi-transmissive and semi-reflective electrode 452 which function as a micro optical resonator (microcavity). Note that the reflective electrode 451 is formed using a conductive material having reflectivity, and a film whose visible light reflectivity is 40% to 100%, preferably 70% to 100%, and whose resistivity is $1\times10^{-2}$ Ωcm or lower is used. In addition, the semi-transmissive and semi-reflective electrode 452 is formed using a conductive material having reflectivity and a conductive material having a light-transmitting property, and a film whose visible light reflectivity is 20% to 80%, preferably 40% to 70%, and whose resistivity is $1\times10^{-2}$ Ωcm or lower is used.

In this embodiment, the thicknesses of the transparent conductive layers (the first transparent conductive layer 453a and the second transparent conductive layer 453b) provided in the first light-emitting element 450R and the second light-emitting element 450G, respectively, are varied between the light-emitting elements, whereby the light-emitting elements differ in the optical path length from the reflective electrode 451 to the semi-transmissive and semi-reflective electrode 452. In other words, in light having a broad emission spectrum, which is emitted from the light-emitting layers of each of the light-emitting elements, light with a wavelength that is resonated between the reflective electrode 451 and the semi-transmissive and semi-reflective electrode 452 can be enhanced while light with a wavelength that is not resonated therebetween can be attenuated. Thus, when the elements differ in the optical path length from the reflective electrode 451 to the semi-transmissive and semi-reflective electrode 452, light with different wavelengths can be extracted.

Note that the optical path length (also referred to as optical distance) is expressed as a product of an actual distance and a refractive index, and in this embodiment, is a product of an actual thickness and n (refractive index). That is, the following relation is satisfied: optical path length=actual thickness×n.

Further, the optical path length from the reflective electrode 451 to the semi-transmissive and semi-reflective electrode 452 is set to $m\lambda_R/2$ (m is a natural number of 1 or more) in the first light-emitting element 450R; the optical path length from the reflective electrode 451 to the semi-transmissive and semi-reflective electrode 452 is set to $l\lambda_G/2$ (l is a natural number of 1 or more) in the second light-emitting element 450G; and the optical path length from the reflective electrode 451 to the semi-transmissive and semi-reflective electrode 452 is set to $n\lambda_B/2$ (n is a natural number of 1 or more) in the third light-emitting element 450B.

In this manner, the light ($\lambda_R$) emitted from the first light-emitting layer 454R included in the EL layer 455 is mainly extracted from the third light-emitting element 450R, the light ($\lambda_G$) emitted from the second light-emitting layer 454G included in the EL layer 455 is mainly extracted from the second light-emitting element 450G, and the light ($\lambda_B$) emitted from the third light-emitting layer 454B included in the EL layer 455 is mainly extracted from the third light-emitting element 450B. Note that the light extracted from each of the light-emitting elements is emitted through the semi-transmissive and semi-reflective electrode 452 side.

Further, strictly speaking, the optical path length from the reflective electrode 451 to the semi-transmissive and semi-reflective electrode 452 can be the distance from a reflection region in the reflective electrode 451 to a reflection region in the semi-transmissive and semi-reflective electrode 452. However, it is difficult to precisely determine the positions of the reflection regions in the reflective electrode 451 and the semi-transmissive and semi-reflective electrode 452, and the above effect can be sufficiently obtained wherever the reflection regions may be set in the reflective electrode 451 and the semi-transmissive and semi-reflective electrode 452.

Next, the optical path length from the reflective electrode 451 to the third light-emitting layer 454R is adjusted to $(2n_R-1)\lambda_R/4$ ($n_R$ is a natural number of 1 or more) because in the first light-emitting element 450R, light (first reflected light) that is reflected by the reflective electrode 451 of the light emitted from the third light-emitting layer 454R interferes with light (first incident light) that directly enters the semi-transmissive and semi-reflective electrode 452 from the third light-emitting layer 454R. By adjusting the optical path length, the phases of the first reflected light and the first incident light can be aligned with each other and the light emitted from the third light-emitting layer 454R can be amplified.

Note that, strictly speaking, the optical path length from the reflective electrode 451 to the third light-emitting layer 454R can be the optical path length from a reflection region in the reflective electrode 451 to a light-emitting region in the third light-emitting layer 454R. However, it is difficult to precisely determine the positions of the reflection region in the reflective electrode 451 and the light-emitting region in the third light-emitting layer 454R, and the above effect can be sufficiently obtained wherever the reflection region and the light-emitting region may be set in the reflective electrode 451 and the third light-emitting layer 454R, respectively.

Next, the optical path length from the reflective electrode 451 to the second light-emitting layer 454G is adjusted to $(2n_G-1)\lambda_G/4$ ($n_G$ is a natural number of 1 or more) because in the second light-emitting element 450G, light (second reflected light) that is reflected by the reflective electrode 451 of the light emitted from the second light-emitting layer 454G interferes with light (second incident light) that directly enters the semi-transmissive and semi-reflective electrode 452 from the second light-emitting layer 454G. By adjusting the optical path length, the phases of the second reflected light and the second incident light can be aligned with each other and the light emitted from the second light-emitting layer 454G can be amplified.

Note that, strictly speaking, the optical path length from the reflective electrode 451 to the second light-emitting layer 454G can be the optical path length from a reflection region in the reflective electrode 451 to a light-emitting region in the second light-emitting layer 454G. However, it is difficult to precisely determine the positions of the reflection region in the reflective electrode 451 and the light-emitting region in the second light-emitting layer 454G, and the above effect can be sufficiently obtained wherever the reflection region and the light-emitting region may be set in the reflective electrode 451 and the second light-emitting layer 454G, respectively.

Next, the optical path length from the reflective electrode 451 to the first light-emitting layer 454B is adjusted to $(2n_B-1)\lambda_B/4$ ($n_B$ is a natural number of 1 or more) because in the third light-emitting element 450B, light (third reflected light) that is reflected by the reflective electrode 451 of the light emitted from the third light-emitting layer 454B interferes with light (third incident light) that directly enters the semi-transmissive and semi-reflective electrode 452 from the first light-emitting layer 454B. By adjusting the optical path length, the phases of the third reflected light and the third incident light can be aligned with each other and the light emitted from the first light-emitting layer 454B can be amplified.

Note that, strictly speaking, the optical path length from the reflective electrode 451 to the first light-emitting layer 454B can be the optical path length from a reflection region in the reflective electrode 451 to a light-emitting region in the first light-emitting layer 454B. However, it is difficult to precisely determine the positions of the reflection region in the reflective electrode 451 and the light-emitting region in the first light-emitting layer 454B; therefore, it is assumed that the above effect can be sufficiently obtained wherever the reflection region and the light-emitting region may be set in the reflective electrode 451 and the first light-emitting layer 454B, respectively.

Note that although each of the light-emitting elements in the above-described structure includes one EL layer, the present invention is not limited thereto; for example, the structure of the tandem (stacked type) light-emitting element which is described in Embodiment 3 can be combined, in which case a plurality of light-emitting layers is provided so that a charge generation layer is interposed therebetween in one light-emitting element.

The light-emitting device described in this embodiment has a microcavity structure, in which light with wavelengths which differ depending on the light-emitting elements can be extracted even when they include the same light-emitting layers, so that it is not necessary to form different light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

Note that the structure described in this embodiment can be combined as appropriate with any of the structures described in the other embodiments.

(Embodiment 5)

In this embodiment, a light-emitting device of one embodiment of the present invention will be described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 5A and 5B.

Figure 5A:
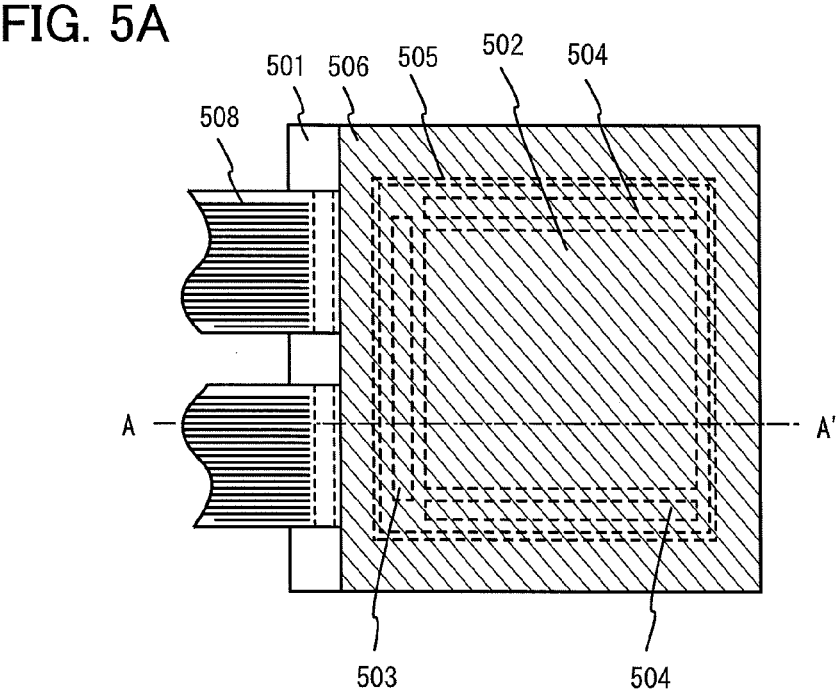
FIGS. 5A and 5B illustrate a light-emitting device of one embodiment of the present invention.
Figure 5B:
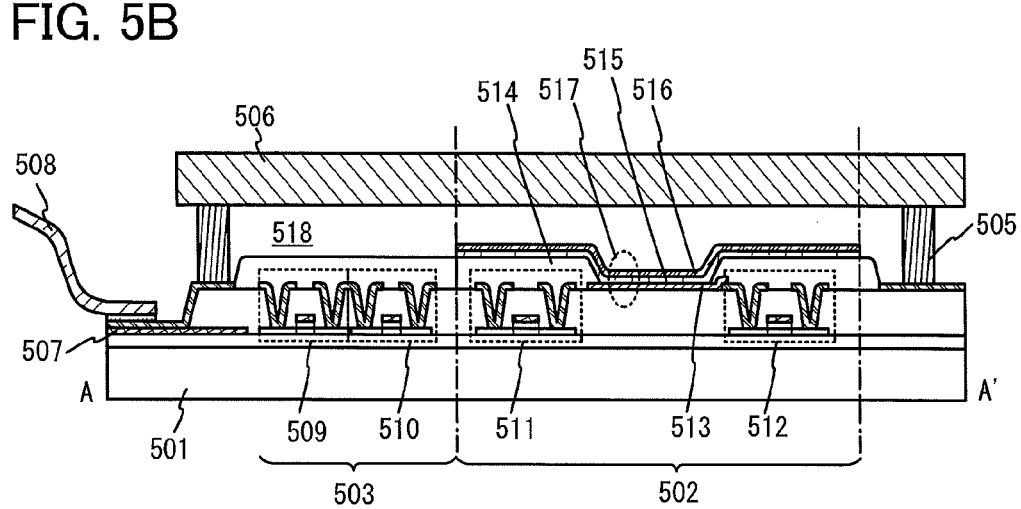

Note that FIG. 5A is a top view illustrating a light-emitting device and FIG. 5B is a cross-sectional view taken along the dotted line A-A' in FIG. 5A. The active matrix light-emitting device according to this embodiment includes a pixel portion 502 provided over an element substrate 501, a driver circuit portion (a source line driver circuit) 503, and driver circuit portions (gate line driver circuits) 504. The pixel portion 502, the driver circuit portion 503, and the driver circuit portions 504 are sealed with a sealant 505 between the element substrate 501 and a sealing substrate 506.

In addition, over the element substrate 501, a lead wiring 507 for connecting an external input terminal, through which a signal (e.g., a video signal, a clock signal, a start signal, a reset signal, or the like) or electric potential from the outside is transmitted to the driver circuit portion 503 and the driver circuit portions 504, is provided. Here, an example in which a flexible printed circuit (FPC) 508 is provided as the external input terminal is described. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure is described with reference to FIG. 5B. The driver circuit portion and the pixel portion are formed over the element substrate 501, and the driver circuit portion 503 which is the source line driver circuit and the pixel portion 502 are illustrated.

An example in which a CMOS circuit which is a combination of an n-channel TFT 509 and a p-channel TFT 510 is formed as the driver circuit portion 503 is illustrated. Note that a circuit included in the driver circuit portion may be formed using any of various circuits, such as a CMOS circuit, a PMOS circuit, or an NMOS circuit. In this embodiment, although a driver-integrated type structure in which a driver circuit is formed over a substrate is described, a driver circuit is not necessarily formed over a substrate but can be formed outside a substrate.

The pixel portion 502 is formed of a plurality of pixels each of which includes a switching TFT 511, a current control TFT 512, and a first electrode 513 which is electrically connected to a wiring (a source electrode or a drain electrode) of the current control TFT 512. An insulator 514 is formed so as to cover an edge portion of the first electrode 513. In this embodiment, the insulator 514 is formed using a positive photosensitive acrylic resin. Note that the first electrode 513 is used as an anode in this embodiment.

In addition, in order to obtain favorable coverage with a film which is to be stacked over the insulator 514, the insulator 514 is preferably formed so as to have a curved surface with curvature at an upper edge portion or a lower edge portion. For example, in the case of using a positive photosensitive acrylic resin as a material for the insulator 514, the insulator 514 is preferably formed so as to have a curved surface with a curvature radius (0.2 μm to 3 μm) at the upper edge portion. Note that the insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode 516 are stacked over the first electrode 513. In the EL layer 515, at least a hole-transport layer and a light-emitting layer are provided. For the hole-transport layer and the light-emitting layer, those described in Embodiment 1 or 2 can be used. Note that in this embodiment, the second electrode 516 is used as a cathode.

A light-emitting element 517 is formed of a stacked structure of the first electrode 513, the EL layer 515, and the second electrode 516. For the first electrode 513, the EL layer 515, and the second electrode 516, the materials described in Embodiment 2 can be used. Although not illustrated, the second electrode 516 is electrically connected to an FPC 508 which is an external input terminal.

In addition, although the cross-sectional view of FIG. 5B illustrates only one light-emitting element 517, a plurality of light-emitting elements are arranged in matrix in the pixel portion 502. Light-emitting elements that emit light of three kinds of colors (R, G, and B) are selectively formed in the pixel portion 502, whereby a light-emitting device capable of full color display can be obtained. Alternatively, a light-emitting device which is capable of full color display may be manufactured by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. Note that the space 518 may be filled with an inert gas (such as nitrogen and argon) or the sealant 505.

An epoxy-based resin is preferably used for the sealant 505. Such a material preferably allows as little moisture and oxygen as possible to penetrate. As the sealing substrate 506, a plastic substrate formed of fiberglass-reinforced plastics (FRP), polyvinyl fluoride (PVF), polyester, acrylic resin, or the like can be used besides a glass substrate or a quartz substrate.

As described above, an active matrix light-emitting device can be obtained.

Note that the structure described in this embodiment can be combined as appropriate with any of the structures described in the other embodiments.

(Embodiment 6)

In this embodiment, an electronic device which partly includes the light-emitting device of one embodiment of the present invention which is described in the above embodiments will be described. Examples of the electronic device include cameras such as video cameras and digital cameras, goggle type displays, navigation systems, audio replay devices (e.g., car audio systems and audio systems), computers, game machines, portable information terminals (e.g., mobile computers, mobile phones, smartphones, portable game machines, e-book readers, and tablet terminals), and image replay devices in which a recording medium is provided (specifically, devices that are capable of replaying recording media such as digital versatile discs (DVDs) and equipped with a display device that can display an image). Specific examples of these electronic devices will be described with reference to FIGS. 6A to 6D and FIGS. 7A to 7D.

Figure 6A:
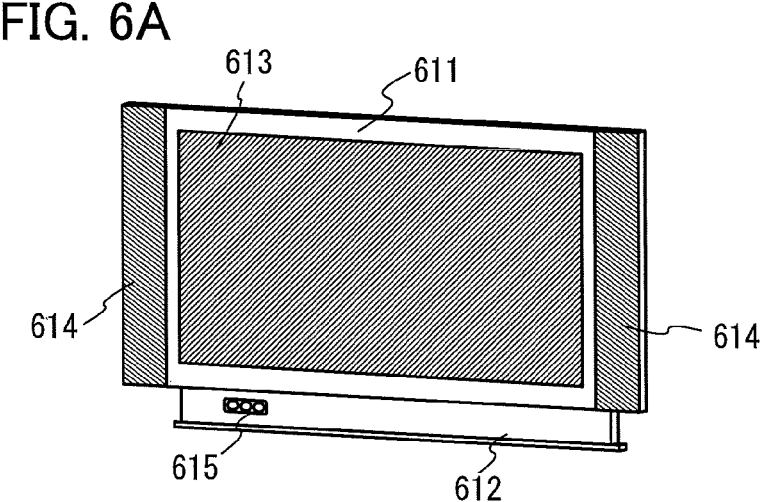
FIGS. 6A to 6D each illustrate an electronic device of one embodiment of the present invention.

FIG. 6A illustrates a television set according to one embodiment of the present invention, which includes a housing 611, a supporting base 612, a display portion 613, speaker portions 614, video input terminals 615, and the like. In this television set, the light-emitting device of one embodiment of the present invention can be applied to the display portion 613. Since the light-emitting device of one embodiment of the present invention is driven at low voltage and has high current efficiency, by the application of the light-emitting device of one embodiment of the present invention, a television set with reduced power consumption can be obtained.

Figure 6B:
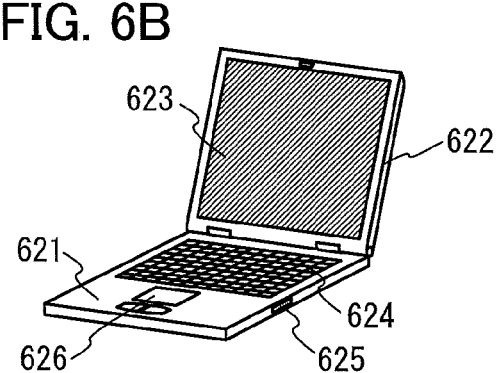

FIG. 6B illustrates a computer according to one embodiment of the present invention, which includes a main body 621, a housing 622, a display portion 623, a keyboard 624, an external connection port 625, a pointing device 626, and the like. In this computer, the light-emitting device of one embodiment of the present invention can be applied to the display portion 623. Since the light-emitting device of one embodiment of the present invention is driven at low voltage and has high current efficiency, by the application of the light-emitting device of one embodiment of the present invention, a computer with reduced power consumption can be obtained.

Figure 6C:
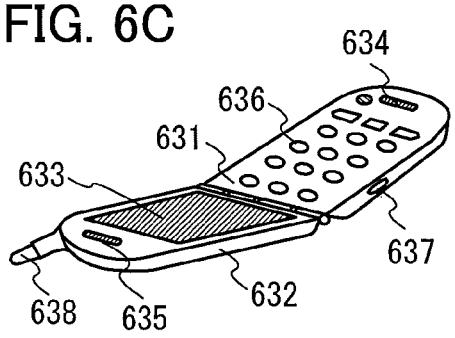

FIG. 6C illustrates a mobile phone according to one embodiment of the present invention, which includes a main body 631, a housing 632, a display portion 633, an audio input portion 634, an audio output portion 635, operation keys 636, an external connection port 637, an antenna 638, and the like. In this mobile phone, the light-emitting device of one embodiment of the present invention can be applied to the display portion 633. Since the light-emitting device of one embodiment of the present invention is driven at low voltage and has high current efficiency, by the application of the light-emitting device of one embodiment of the present invention, a mobile phone with reduced power consumption can be obtained.

Figure 6D:
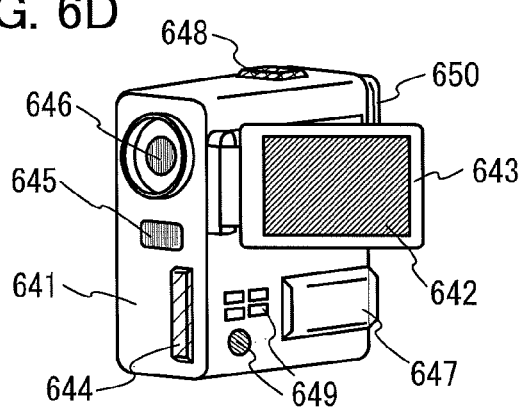

FIG. 6D illustrates a camera according to one embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of one embodiment of the present invention can be applied to the display portion 642. Since the light-emitting device of one embodiment of the present invention is driven at low voltage and has high current efficiency, by the application of the light-emitting device of one embodiment of the present invention, a camera with reduced power consumption can be obtained.

Figure 7A:
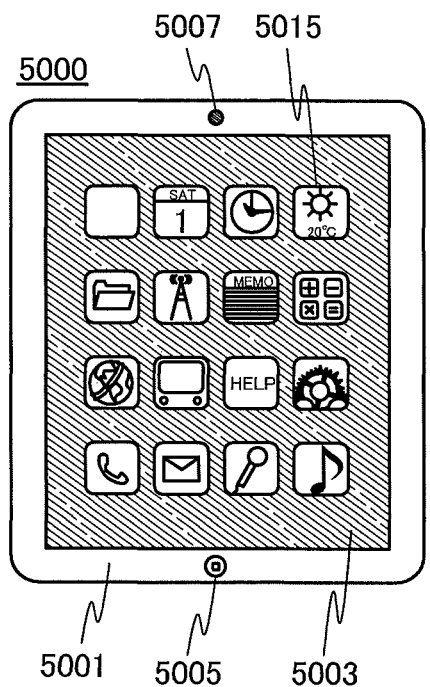
FIGS. 7A-7C and 7D each illustrate a mobile terminal of one embodiment of the present invention.
Figure 7B:
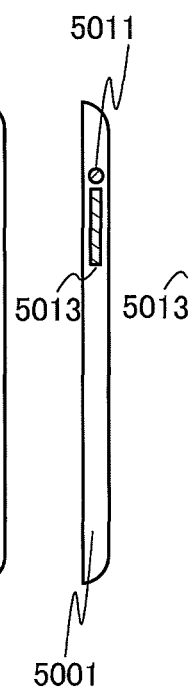
Figure 7C:
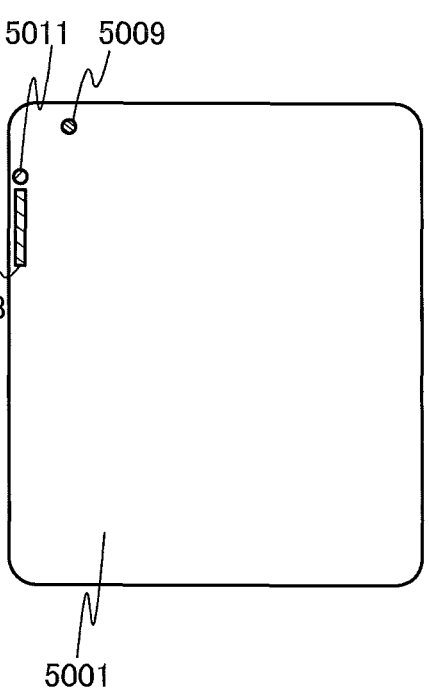
Figure 7D:
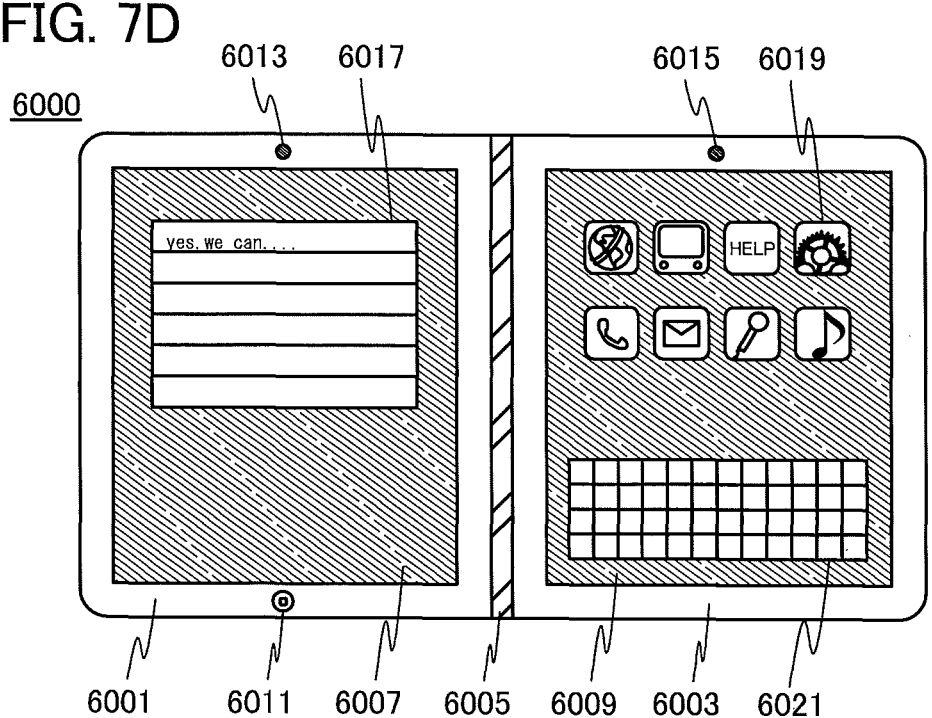

FIGS. 7A to 7D illustrate examples of mobile terminals according to one embodiment of the present invention. FIGS. 7A, 7B, and 7C illustrate a mobile terminal 5000, and FIG. 7D illustrates a mobile terminal 6000.

FIGS. 7A, 7B, and 7C are a front view, a side view, and a rear view of the mobile terminal 5000, respectively. FIG. 7D is a front view of the mobile terminal 6000.

The mobile terminal 5000 includes a housing 5001, a display portion 5003, a power button 5005, a front camera 5007, a rear camera 5009, a first external connection terminal 5011, a second external connection terminal 5013, and the like.

In addition, the display portion 5003 is incorporated in the housing 5001 and can be used as a touch panel. For example, e-mailing or schedule management can be performed by touching an icon 5015 and the like on the display portion 5003. Further, the front camera 5007 is incorporated on the front side of the housing 5001, whereby an image on the user's side can be taken. The rear camera 5009 is incorporated in the rear side of the housing 5001, whereby an image on the opposite side of the user can be taken. Further, the housing 5001 includes the first external connection terminal 5011 and the second external connection terminal 5013. For example, sound can be output to an earphone or the like through the first external connection terminal 5011, and data can be moved through the second external connection terminal 5013.

The mobile terminal 6000 in FIG. 7D includes a first housing 6001, a second housing 6003, a hinge portion 6005, a first display portion 6007, a second display portion 6009, a power button 6011, a first camera 6013, a second camera 6015, and the like.

The first display portion 6007 is incorporated in the first housing 6001. The second display portion 6009 is incorporated in the second housing 6003. For example, the first display portion 6007 and the second display portion 6009 are used as a display panel and a touch panel, respectively. A user can select images, enter characters, and so on by touching an icon 6019 displayed on the second display portion 6009 or a keyboard 6021 (actually, a keyboard image displayed on the second display portion 6009) while looking at a text icon 6017 displayed on the first display portion 6007. Alternatively, the first display portion 6007 and the second display portion 6009 may be a touch panel and a display panel, respectively; the first display portion 6007 and the second display portion 6009 may be touch panels.

The first housing 6001 and the second housing 6003 are connected to each other and open and close on the hinge portion 6005. In such a structure, the first display portion 6007 incorporated in the first housing 6001 and the second display portion 6009 incorporated in the second housing 6003 are preferably made to face each other, in which case the surfaces of the first display portion 6007 and the second display portion 6009 (e.g., plastic substrates) can be protected when the mobile terminal 6000 is carried.

Alternatively, the first housing 6001 and the second housing 6003 may be separated by the hinge portion 6005 (so-called convertible type). Thus, the application range of the mobile terminal 6000 can be extended: for example, the first housing 6001 is used in a vertical orientation and the second housing 6003 is used in a horizontal orientation.

Further, the first camera 6013 and the second camera 6015 can take 3D images.

The mobile terminal 5000 and the mobile terminal 6000 may send and receive data wirelessly. For example, through wireless internet connection, desired data can be purchased and downloaded.

The mobile terminals 5000 and 6000 can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs). A detector such as a photodetector capable of optimizing display luminance in accordance with the amount of outside light or a sensor for detecting inclination, like a gyroscope or an acceleration sensor, can be included.

The light-emitting device of one embodiment of the present invention can be applied to the display portion 5003 of the mobile terminal 5000, the first display portion 6007 of the mobile terminal 6000, and/or the second display portion 6009 of the mobile terminal 6000. Since the light-emitting device of one embodiment of the present invention is driven at low voltage and has high current efficiency, by the application of the light-emitting device of one embodiment of the present invention, a tablet terminal with reduced power consumption can be obtained.

As described above, the applicable range of the light-emitting device of one embodiment of the present invention is so wide that the light-emitting device can be applied to electronic devices in a variety of fields. With the use of the light-emitting device of one embodiment of the present invention, an electronic device with reduced power consumption can be obtained.

The light-emitting device of one embodiment of the present invention can also be used as a lighting device. Specific examples of the lighting device are described with reference to FIGS. 8A to 8C.

Figure 8A:
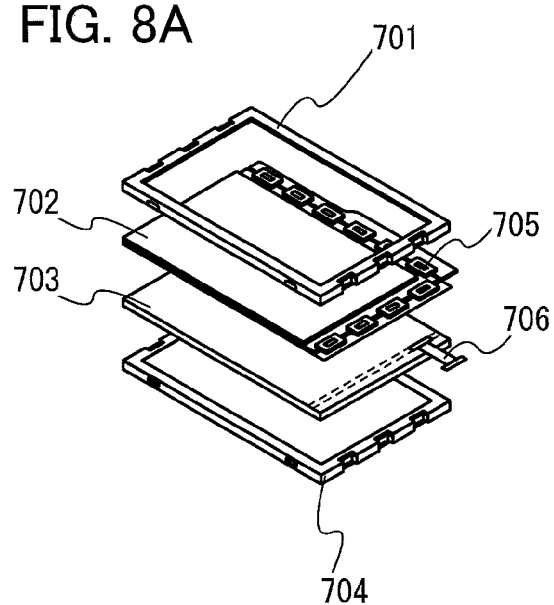
FIGS. 8A to 8C each illustrate a lighting device of one embodiment of the present invention.

FIG. 8A illustrates an example of a liquid crystal display device using the light-emitting device of one embodiment of the present invention as a backlight. The liquid crystal display device illustrated in FIG. 8A includes a housing 701, a liquid crystal panel 702, a backlight 703, and a housing 704. The liquid crystal panel 702 is connected to a driver IC 705. The light-emitting device of one embodiment of the present invention is used as the backlight 703, and current is supplied through a terminal 706. By using the light-emitting device of one embodiment of the present invention as a backlight of a liquid crystal display device as described above, a backlight with low power consumption can be obtained. Moreover, since the light-emitting device of one embodiment of the present invention is a lighting device for surface light emission and the enlargement of the light-emitting device is possible, the backlight can be made larger. Thus, a larger-area liquid crystal display device with low power consumption can be obtained.

Figure 8B:
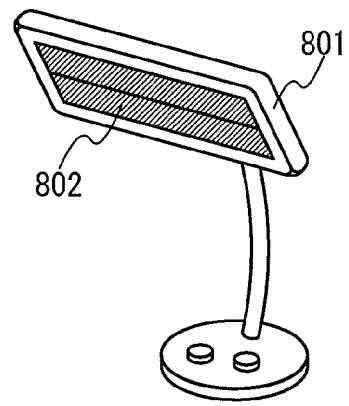

Next, FIG. 8B illustrates an example in which the light-emitting device of one embodiment of the present invention is used for a desk lamp which is a lighting device. The desk lamp illustrated in FIG. 8B includes a housing 801 and a light source 802, and the light-emitting device of one embodiment of the present invention is used as the light source 802. Since the light-emitting device of one embodiment of the present invention is driven at low voltage and has high current efficiency, by the application of the light-emitting device of one embodiment of the present invention, a desk lamp with reduced power consumption can be obtained.

Figure 8C:
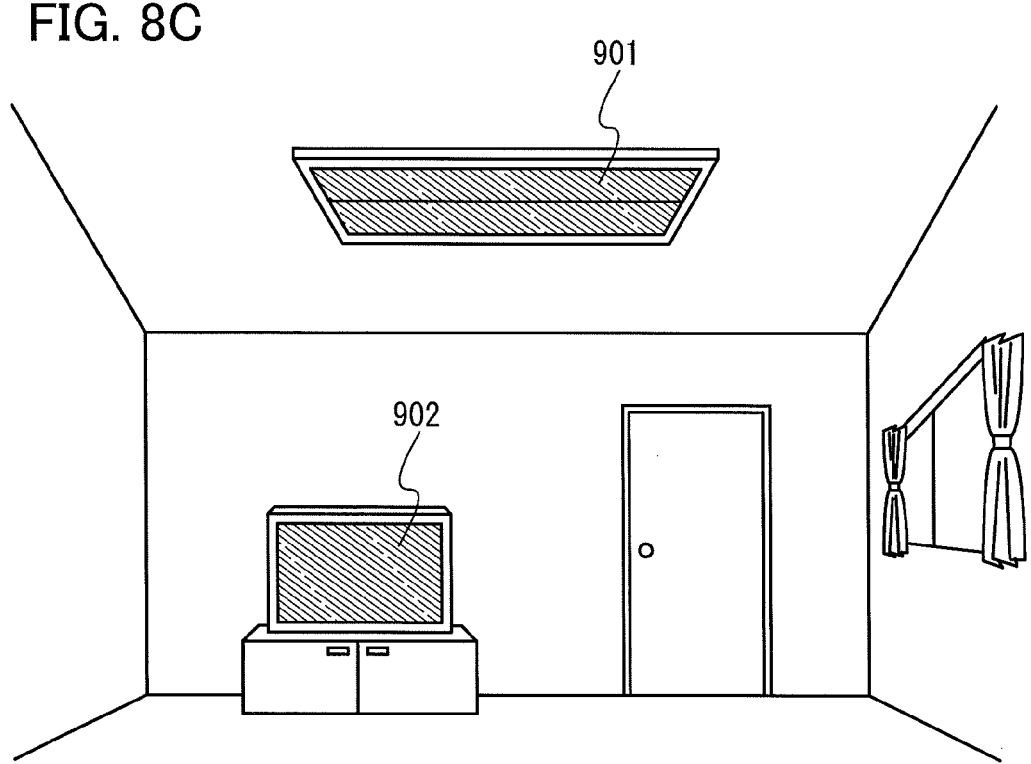

FIG. 8C illustrates an example in which the light-emitting device of one embodiment of the present invention is used for an indoor lighting device 901. Since the light-emitting device of an embodiment of the present invention can also have a larger area, the light-emitting device of an embodiment of the present invention can be used as a lighting system having a large area. Since the light-emitting device of one embodiment of the present invention is driven at low voltage and has high current efficiency, by the application of the light-emitting device of one embodiment of the present invention, a lighting device with reduced power consumption can be obtained. In a room where the light-emitting device of one embodiment of the present invention is used for the indoor lighting device 901 as described above, a television set 902 of one embodiment of the present invention as described with reference to FIG. 6A can be installed so that public broadcasting and movies can be watched.

Note that this embodiment can be combined with any of the other embodiments as appropriate.

EXAMPLE 1

In this example, examples of methods for synthesizing organic compounds represented by Structural Formula (100), Structural Formula (101), and Structural Formula (110) described in Embodiment 1 will be described below.

Method for Synthesizing 9-[4-(9-phenyl-9H-fluoren-9-yl)phenyl]-9H-carbazole (abbreviation: CzFLP) Represented by Structural Formula (100)

First, a method for synthesizing CzFLP (abbreviation) represented by Structural Formula (100) will be described.

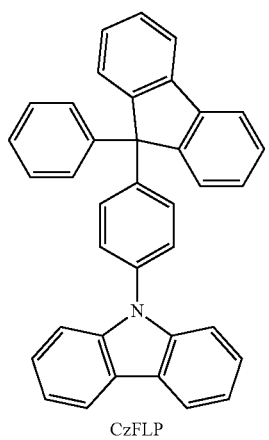

CzFLP

Into a 50-mL three-neck flask were put 2.0 g (5.0 mmol) of 9-(4-bromophenyl)-9-phenyl-9H-fluorene, 0.8 g (5.0 mmol) of carbazole, 0.7 g (7.0 mmol) of sodium tert-butoxide (tBuONa), and 28 mg (50 μmol) of bis(dibenzylideneacetone)palladium(0) (Pd(dba)$_2$), and the air in the flask was replaced with nitrogen. Then, 20 mL of dehydrated xylene was added to this mixture. After the mixture was deaerated while being stirred under reduced pressure, 0.2 mL (0.1 mmol) of tri(tert-butyl)phosphine((tBu)$_3$P) (10 wt % hexane solution) was added thereto. This mixture was stirred under a nitrogen atmosphere at 110° C. for 5.5 hours to be reacted.

After the reaction, 400 mL of toluene was added to this reaction mixture, and this suspension was filtrated through Florisil, alumina, and Celite. The resulting filtrate was concentrated, purified by silica gel column chromatography (a developing solvent: a mixed solution of toluene and hexane), and then recrystallized to give 4.4 g of white powder which is a target substance in a yield of 91%. A reaction scheme of the above synthesis method is shown in the following (B-1).

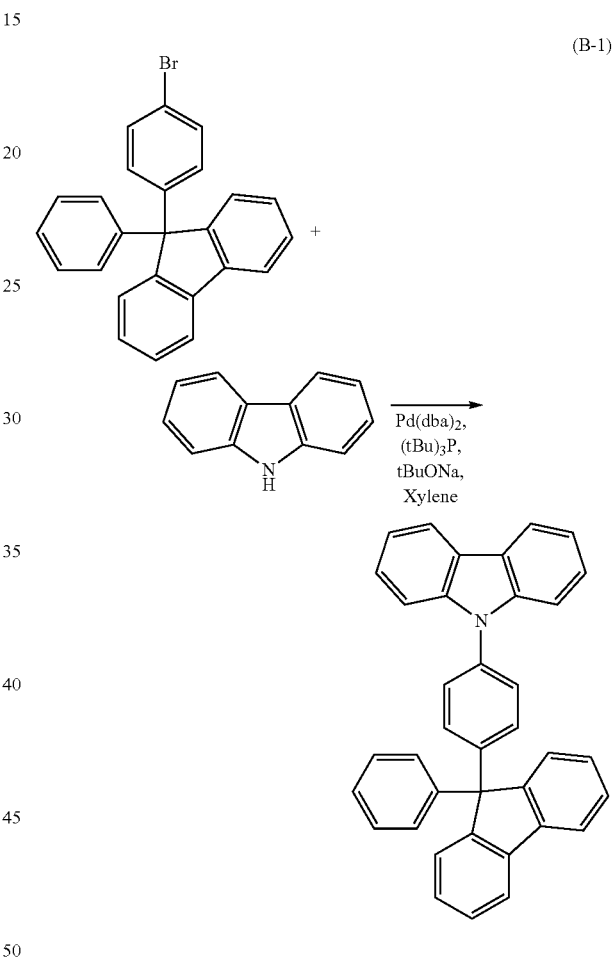

The Rf values of the target substance, 9-(4-bromophenyl)-9-phenyl-9H-fluorene, and carbazole were respectively 0.28, 0.38, and 0.10, which were found by silica gel thin layer chromatography (TLC) (a developing solvent: ethyl acetate and hexane in a 1:10 ratio).

The compound obtained by Reaction Scheme (B-1) was measured by a nuclear magnetic resonance ($^1$H NMR) method. The measurement data is shown below.

$^1$H NMR (CDCl$_3$, 300 MHz): δ (ppm)=7.23-7.44 (m, 19H), 7.51 (d, J=6.9 Hz, 2H), 7.81 (d, J=7.8 Hz, 2H), 8.13 (d, J=7.8 Hz, 2H).

Figure 9A:
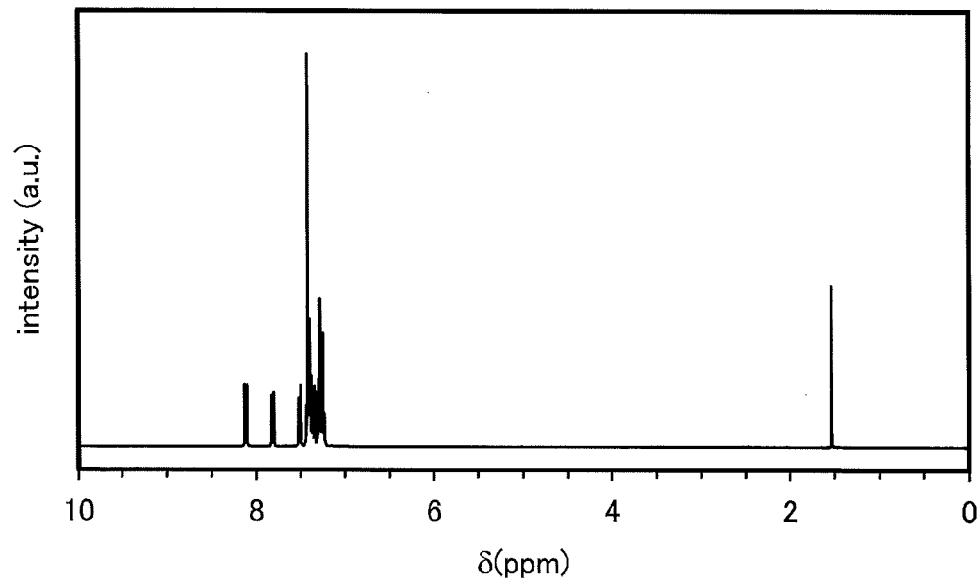
FIGS. 9A and 9B are $^1$H NMR charts of CzFLP (abbreviation).
Figure 9B:
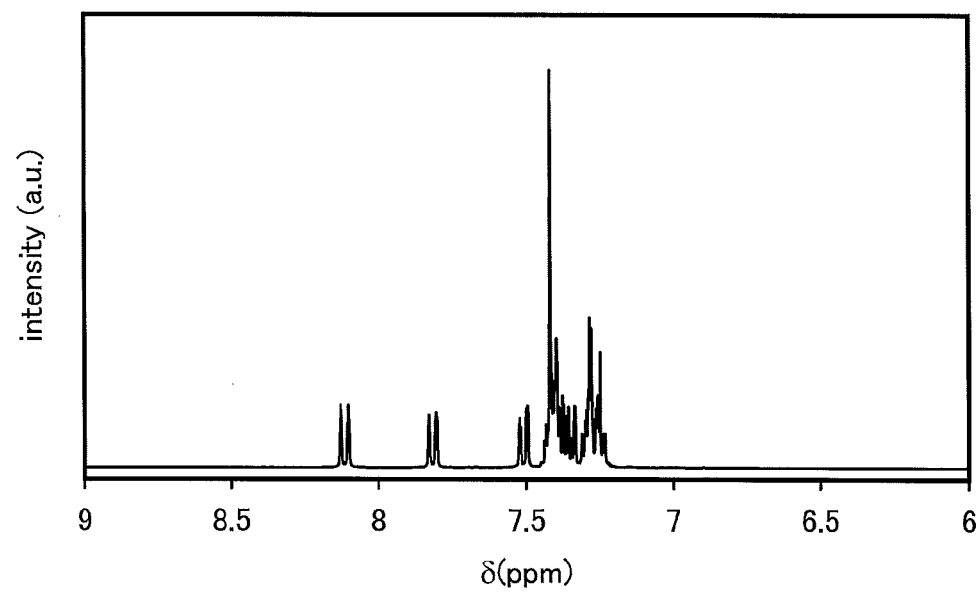

FIGS. 9A and 9B are $^1$H-NMR charts. Note that FIG. 9B is an enlarged chart of FIG. 9A. The measurement results indicate that CzFLP (abbreviation), which was a target substance, was obtained.

Method for Synthesizing 9-[3-(9-phenyl-9H-fluoren-9-yl)phenyl]-9H-carbazole (abbreviation: mCzFLP) Represented by Structural Formula (101)

Next, a method for synthesizing mCzFLP (abbreviation) represented by Structural Formula (101) will be described.

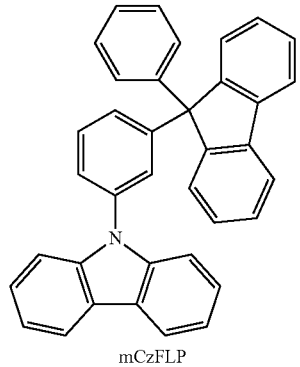

mCzFLP (101)

(C-1)

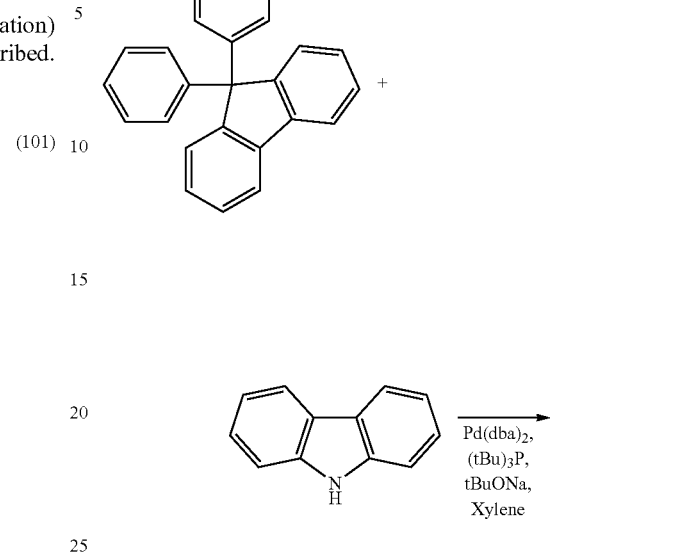

Into a 100-mL three-neck flask were put 4.9 g (12.4 mmol) of 9-(3-bromophenyl)-9-phenylfluorene, 2.1 g (12.4 mmol) of carbazole, and 3.6 g (37.2 mmol) of sodium tert-butoxide (tBuONa), and the air in the flask was replaced with nitrogen. To this mixture were added 31.0 mL of xylene, 0.2 mL of a 10% hexane solution of tri(tert-butyl)phosphine((tBu)$_3$P), and 48.1 mg (0.1 mmol) of bis(dibenzylideneacetone)palladium(0) (Pd(dba)$_2$), and the obtained mixture was stirred at 140° C. for 3.5 hours. After the stirring, 47.7 mg (0.1 mmol) of bis(dibenzylideneacetone)palladium(0) and 0.6 mL of a 10% hexane solution of tri(tert-butyl)phosphine were added, and the obtained mixture was stirred for 1.5 hours.

After the stirring, 70 mL of ethyl acetate and 150 mL of toluene were added, heating was performed, and suction filtration through Florisil, Celite, and alumina was performed to give a filtrate. The resulting filtrate was concentrated to give a solid. The resulting solid was purified by silica gel column chromatography (a developing solvent: hexane and toluene in a 7:3 ratio) to give a white solid which was a target substance. The resulting white solid was recrystallized from a mixed solvent of toluene and hexane to give 2.7 g of a white solid which was a target substance in a yield of 46%.

Then, 1.5 g of the resulting white solid was purified by a train sublimation method. In the purification, the solid was heated at 186° C. under a pressure of 2.7 Pa with a flow rate of argon gas of 5.0 mL/min. After the purification by sublimation, 1.4 g of a white solid which was a target substance was obtained in a yield of 93%. A reaction scheme of the above synthesis method is shown in the following (C-1).

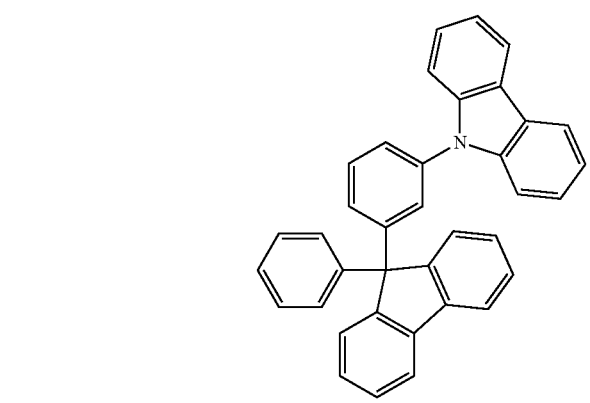

The compound obtained by Reaction Scheme (C-1) was measured by a nuclear magnetic resonance ($^1$H NMR) method. The measurement data is shown below.

$^1$H NMR (CDCl$_3$, 500 MHz): δ=7.19-7.49 (m, 21H), 7.77 (d, J=7.5 Hz, 2H), 8.10 (d, J=7.0 Hz, 2H).

Figure 10A:
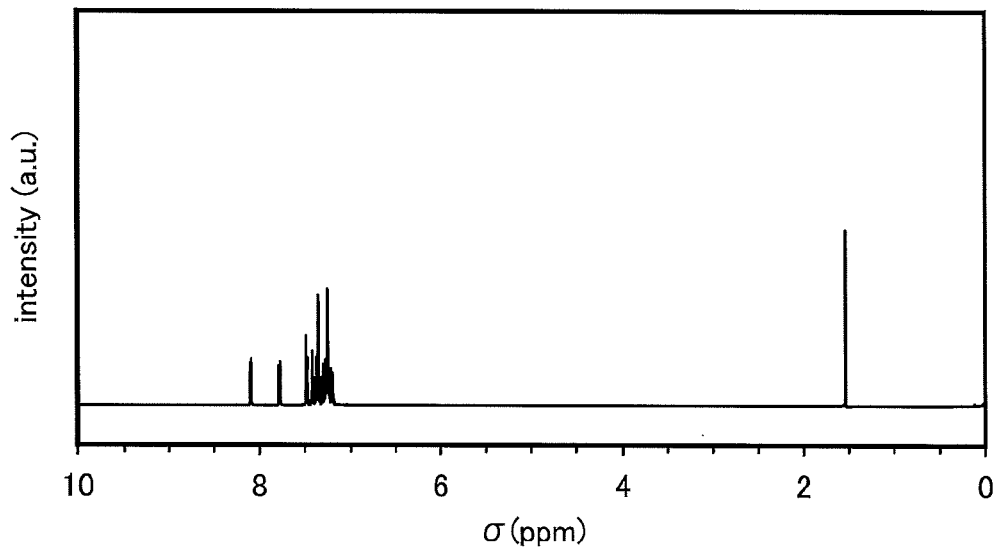
FIGS. 10A and 10B are $^1$H NMR charts of mCzFLP (abbreviation).
Figure 10B:
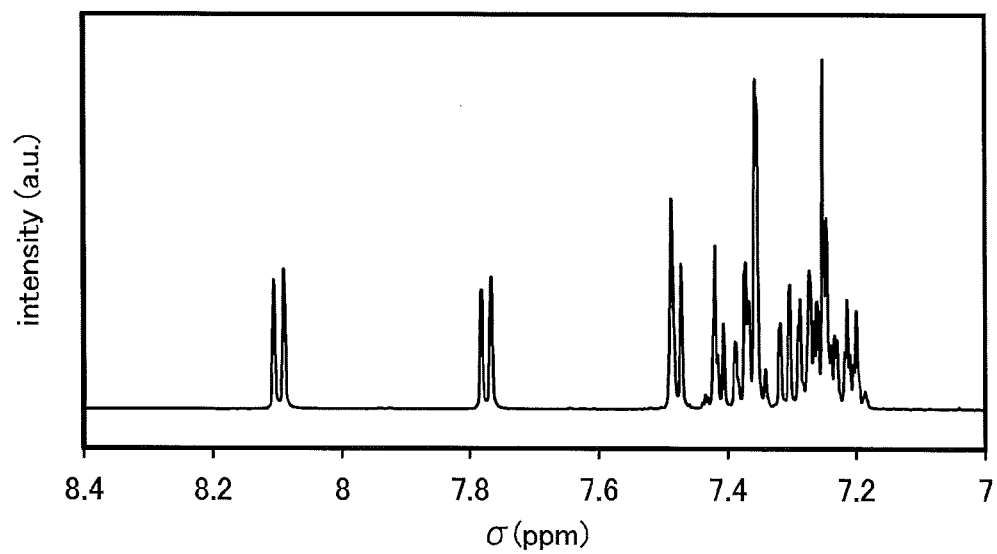

FIGS. 10A and 10B are $^1$H-NMR charts. Note that FIG. 10B is an enlarged chart of FIG. 10A. The measurement results indicate that mCzFLP (abbreviation), which was a target substance, was obtained.

Method for Synthesizing 3-phenyl-9-[4-(9-phenyl-9H-fluoren-9-yl)phenyl]-9H-carbazole (abbreviation: CzFLP-II) Represented by Structural Formula (110)

Next, a method for synthesizing CzFLP-II (abbreviation) represented by Structural Formula (110) will be described.

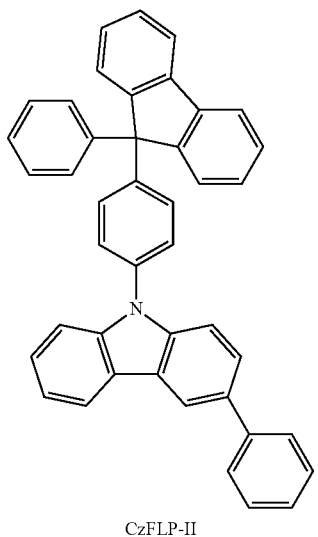

CzFLP-II

Into a 50-mL three-neck flask were put 2.0 g (5.0 mmol) of 9-(4-bromophenyl)-9-phenyl-9H-fluorene, 1.2 g (5.0 mmol) of 3-phenyl-9H-carbazole, 0.7 g (7.0 mmol) of sodium tert-butoxide (tBuONa), and 28 mg (50 μmol) of bis(dibenzylideneacetone)palladium(0) (Pd(dba)$_2$), and the air in the flask was replaced with nitrogen. Then, 20 mL of dehydrated xylene was added to this mixture. After the mixture was deaerated while being stirred under reduced pressure, 0.2 mL (0.1 mmol) of tri(tert-butyl)phosphine ((tBu)$_3$P) (10 wt % hexane solution) was added thereto. This mixture was stirred under a nitrogen atmosphere at 110° C. for 5.5 hours to be reacted.

After the reaction, 200 mL of toluene was added to this reaction mixture, and this suspension was filtered through Florisil, alumina, and Celite. The resulting filtrate was concentrated, purified by silica gel column chromatography (a developing solvent: a mixed solution of toluene and hexane), and then recrystallized to give 4.4 g of white powder which is a target substance in a yield of 91%. A reaction scheme of the above synthesis method is shown in the following (D-1).

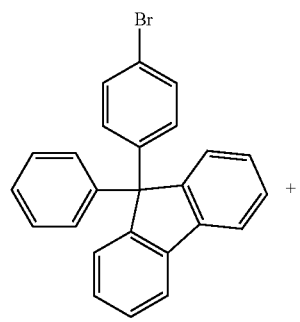

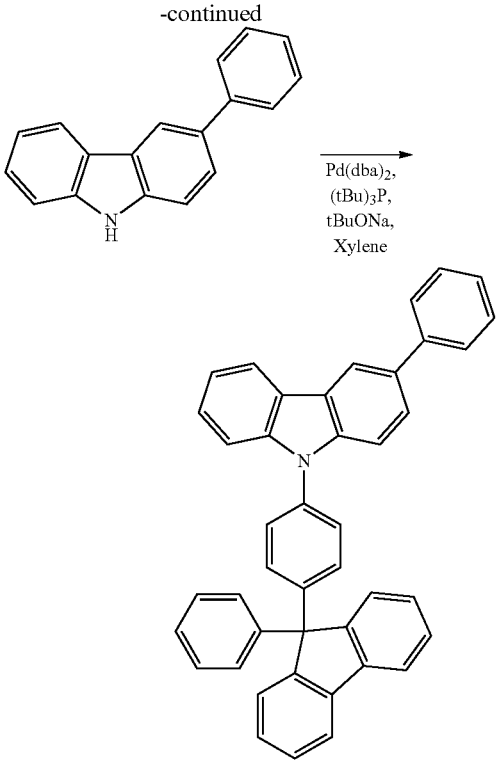

The Rf values of the target substance, 9-(4-bromophenyl)-9-phenyl-9H-fluorene, and 3-phenyl-9H-carbazole were respectively 0.33, 0.58, and 0.11, which were found by silica gel thin layer chromatography (TLC) (a developing solvent: ethyl acetate and hexane in a 1:10 ratio).

The compound obtained by Reaction Scheme (D-1) was measured by a nuclear magnetic resonance ($^1$H NMR) method. The measurement data is shown below.

$^1$H NMR (CDCl$_3$, 300 MHz): δ (ppm)=7.22-7.52 (m, 22H), 7.61 (dd, J=9.0 Hz, 2.1 Hz, 1H), 7.69 (d, J=8.4 Hz, 2H), 7.81 (d, J=7.2 Hz, 2H), 8.15 (d, J=7.8 Hz, 1H), 8.32 (d, J=2.1 Hz, 1H).

Figure 11A:
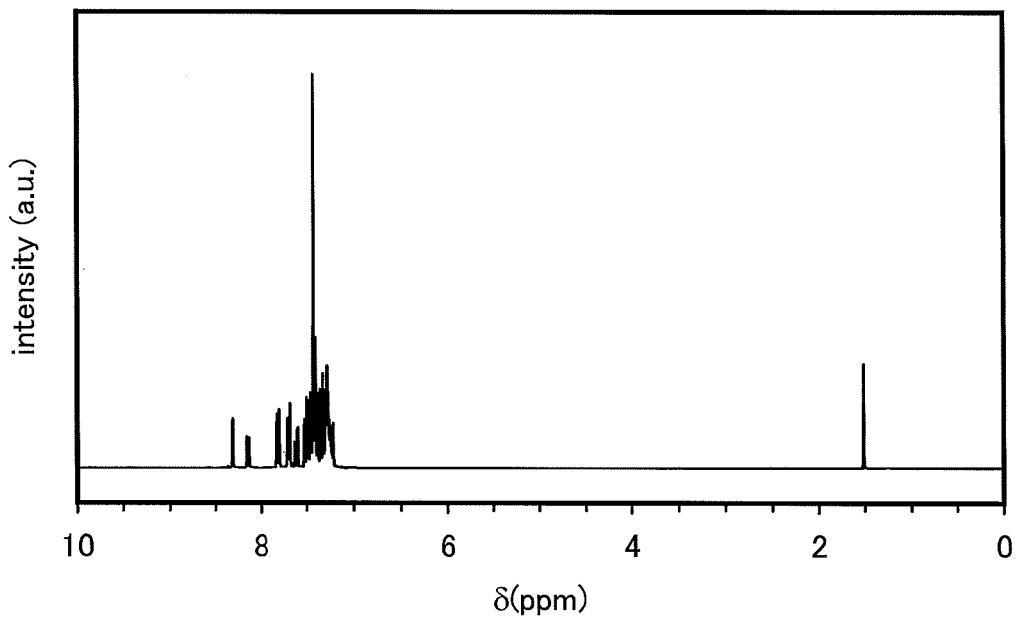
FIGS. 11A and 11B are $^1$H NMR charts of CzFLP-II (abbreviation).
Figure 11B:
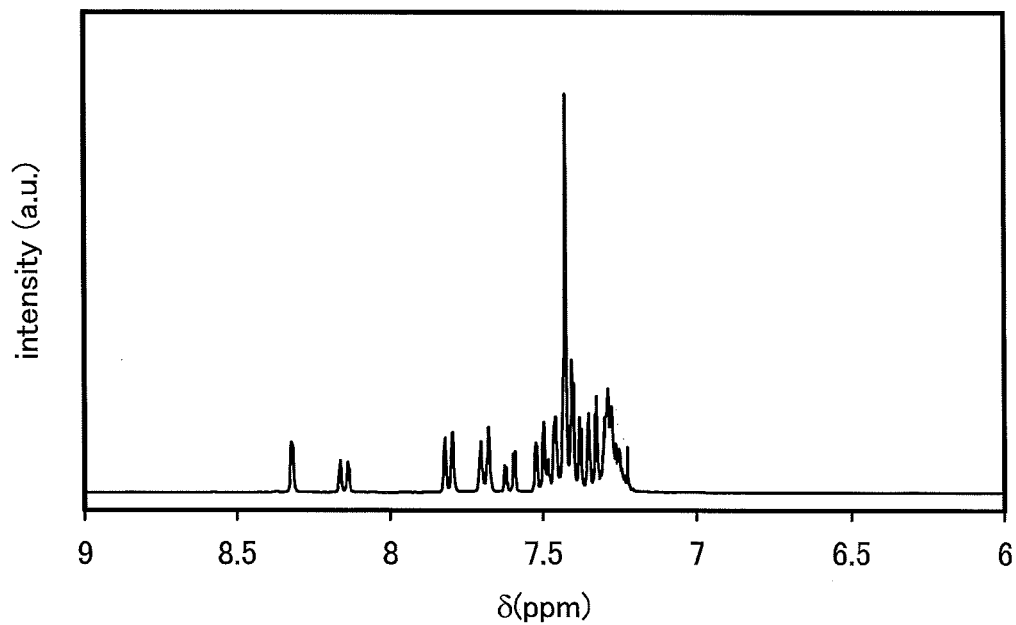

FIGS. 11A and 11B are $^1$H-NMR charts. Note that FIG. 11B is an enlarged chart of FIG. 11A. The measurement results indicate that CzFLP-II (abbreviation), which was a target substance, was obtained.

Furthermore, the glass transition temperature of CzFLP-II (abbreviation) was measured using a differential scanning calorimeter (Pyris 1 DSC, produced by PerkinElmer, Inc.). According to the measurement results, it was found that the glass transition temperature was 131° C. In this manner, it was found that CzFLP-II (abbreviation) has a high glass transition temperature and favorable heat resistance.

EXAMPLE 2

Figure 12:
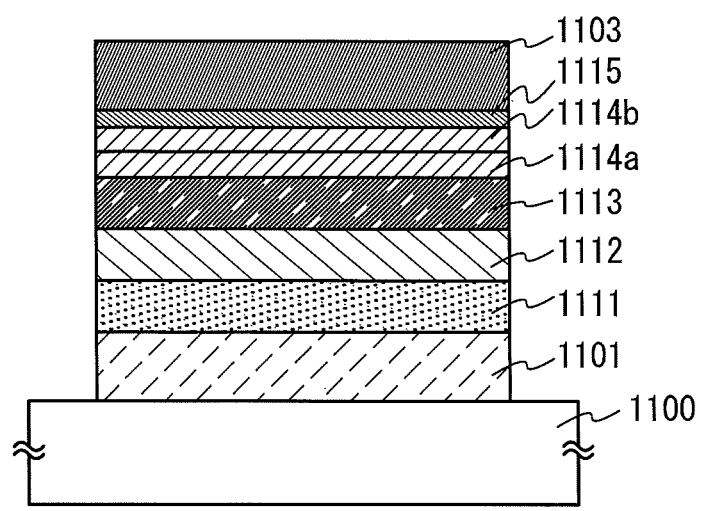
FIG. 12 illustrates each of light-emitting elements in Examples 2 and 3.

In this example, light-emitting elements according to embodiments of the present invention (Light-emitting element 1 and Light-emitting element 2), and a light-emitting element for comparison (Comparative light-emitting element 3) will be described with reference to FIG. 12. Chemical formulae of materials used in this example are shown below.

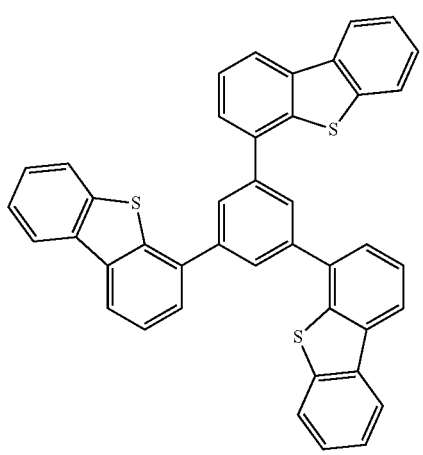
DBT3P-II
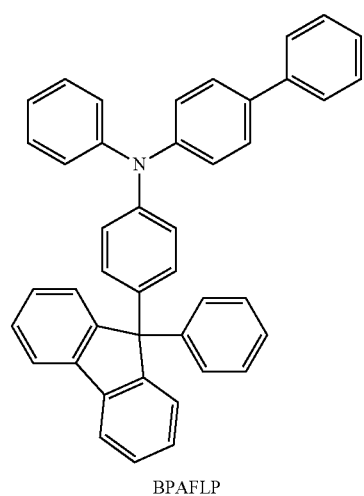
BPAFLP
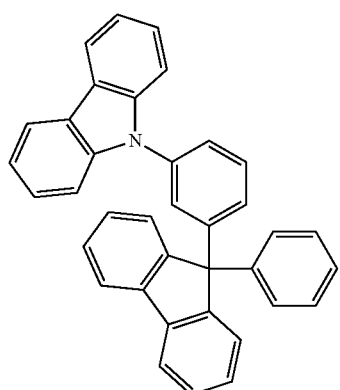
mCzFLP
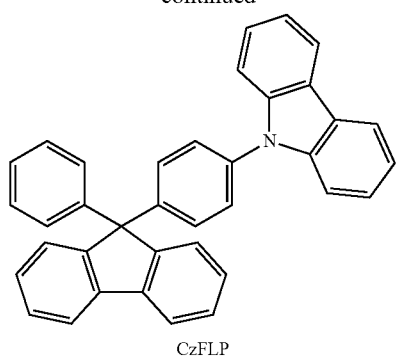
CzFLP
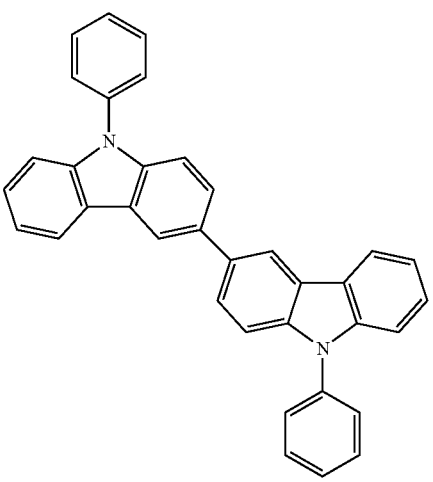
PCCP
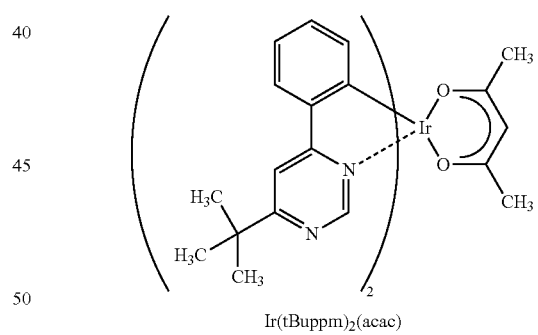
Ir(tBuppm)$_2$(acac)
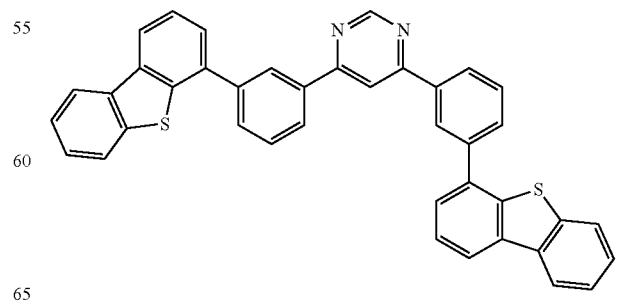
4,6DBTP2Pm-II -continued

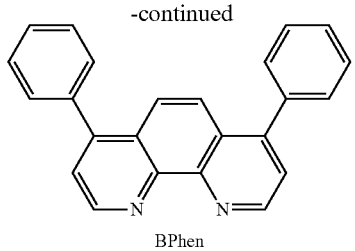

BPhen

Methods for manufacturing Light-emitting elements 1 and 2 of this example and Comparative light-emitting element 3 are described below.
(Light-Emitting Element 1)

First, an indium oxide-tin oxide compound containing silicon or silicon oxide (ITO-SiO$_2$, hereinafter abbreviated to ITSO) was deposited by a sputtering method over a substrate 1100, whereby a first electrode 1101 was formed. Note that the composition ratio of In$_2$O$_3$ to SnO$_2$ and SiO$_2$ in the target used was 85:10:5 [wt %]. The thickness of the first electrode 1101 was 110 nm and the electrode area was 2 mm×2 mm. Here, the first electrode 1101 functions as an anode of the light-emitting element.

Next, as pretreatment for forming the light-emitting element over the substrate 1100, the surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus. Then, the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about 10$^{-4}$ Pa. Then, 4,4',4"-(benzene-1,3,5-triyl)tri(dibenzothiophene) (abbreviation: DBT3P-II) and molybdenum oxide were co-evaporated by an evaporation method using resistance heating to form a hole-injection layer 1111 on the first electrode 1101. The thickness of the hole-injection layer 1111 was set to 40 nm, and the weight ratio of DBT3P-II to molybdenum oxide was adjusted to 2:1 (=DBT3P-II: molybdenum oxide). Note that the co-evaporation method refers to an evaporation method in which evaporation is carried out from a plurality of evaporation sources at the same time in one treatment chamber.

Next, 9-[3-(9-phenyl-9H-fluoren-9-yl)phenyl]-9H-carbazole (abbreviation: mCzFLP) which was synthesized in Example 1 was evaporated over the hole-injection layer 1111, so that a hole-transport layer 1112 was formed. The thickness of the hole-transport layer 1112 was set to 20 nm.

Next, 4,6-bis[3-(4-dibenzothienyl)phenyl]pyrimidine (abbreviation: 4,6mDBTP2Pm-II), 9-phenyl-9H-3-(9-phenyl-9H-carbazol-3-yl)carbazole (abbreviation: PCCP), and (acetylacetonato)bis(6-tert-butyl-4-phenylpyrimidinato) iridium(III) (abbreviation: Ir(tBuppm)$_2$(acac)) were co-evaporated over the hole-transport layer 1112, whereby a light-emitting layer 1113 was formed. Here, the weight ratio of 4,6mDBTP2Pm-II (abbreviation) to PCCP (abbreviation) and Ir(tBuppm)$_2$(acac) (abbreviation) was adjusted to 0.8: 0.2:0.05 (=4,6mDBTP2Pm-II:PCCP:Ir(tBuppm)$_2$(acac)). The thickness of the light-emitting layer 1113 was 40 nm.

Next, a film of 4,6mDBTP2Pm-II (abbreviation) was formed to a thickness of 10 nm over the light-emitting layer 1113, whereby a first electron-transport layer 1114a was formed.

Next, a film of bathophenanthroline (abbreviation: BPhen) was formed to a thickness of 20 nm on the first electron-transport layer 1114a, whereby a second electron-transport layer 1114b was formed.

Next, a film of lithium fluoride (LiF) was formed to a thickness of 1 nm on the second electron-transport layer 1114b by evaporation, whereby an electron-injection layer 1115 was formed.

Lastly, a film of aluminum (Al) was formed to a thickness of 200 nm by evaporation, whereby a second electrode 1103 functioning as a cathode was formed. Thus, Light-emitting element 1 of this example was manufactured.

Note that, in the above evaporation process, evaporation was all performed by a resistance heating method.
(Light-Emitting Element 2)

The structure of Light-emitting element 2 is the same as that of Light-emitting element 1 except for the structure of the hole-transport layer 1112. Only the structure of Light-emitting element 2 which is different from that of Light-emitting element 1 is described below.

9-[4-(9-phenyl-9H-fluoren-9-yl)phenyl]-9H-carbazole (abbreviation: CzFLP) which was synthesized in Example 1 was evaporated over the hole-injection layer 1111, so that the hole-transport layer 1112 was formed. The thickness of the hole-transport layer 1112 was set to 20 nm.
(Comparative Light-Emitting Element 3)

The structure of Comparative light-emitting element 3 is the same as that of Light-emitting element 1 except for the structure of the hole-transport layer 1112. Only the structure of Comparative light-emitting element 3 which is different from that of Light-emitting element 1 is described below.

4-phenyl-4'-(9-phenylfluoren-9-yl)triphenylamine (abbreviation: BPAFLP) was evaporated over the hole-injection layer 1111, whereby the hole-transport layer 1112 was formed. The thickness of the hole-transport layer 1112 was 20 nm.

Table 1 shows element structures of Light-emitting elements 1 and 2 and Comparative light-emitting elements 3 formed as described above.

TABLE 1

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 1 | ITSO 110 nm | DBT3P-II:MoOx (=4:2) 40 nm | mCzFLP 20 nm | 4,6mDBTP2Pm-II:PCCP:Ir(tBuppm)$_2$(acac) (=0.8:0.2:0.05) 40 nm | 4,6mDBTP2Pm-II 10 nm | BPhen 20 nm | LiF 1 nm | Al 200 nm |

TABLE 1-continued

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 2 | ITSO 110 nm | DBT3P-II:MoOx (=4:2) 40 nm | CzFLP 20 nm | 4,6mDBTP2Pm-II:PCCP:Ir(tBuppm)$_2$(acac) (=0.8:0.2:0.05) 40 nm | 4,6mDBTP2Pm-II 10 nm | BPhen 20 nm | LiF 1 nm | Al 200 nm |
| Comparative light-emitting element 3 | ITSO 110 nm | DBT3P-II:MoOx (=4:2) 40 nm | BPAFLP 20 nm | 4,6mDBTP2Pm-II:PCCP:Ir(tBuppm)$_2$(acac) (=0.8:0.2:0.05) 40 nm | 4,6mDBTP2Pm-II 10 nm | BPhen 20 nm | LiF 1 nm | Al 200 nm |

In a glove box containing a nitrogen atmosphere, each of Light-emitting element 1, Light-emitting element 2, and Comparative light-emitting element 3 was sealed with a glass substrate so as not to be exposed to the air (a sealant was applied onto an outer edge of the element and heat treatment was performed at 80° C. for one hour at the time of sealing). After that, operation characteristics of these light-emitting elements were measured. Note that the measurement was carried out at room temperature (in an atmosphere kept at 25° C.).

Figure 13:
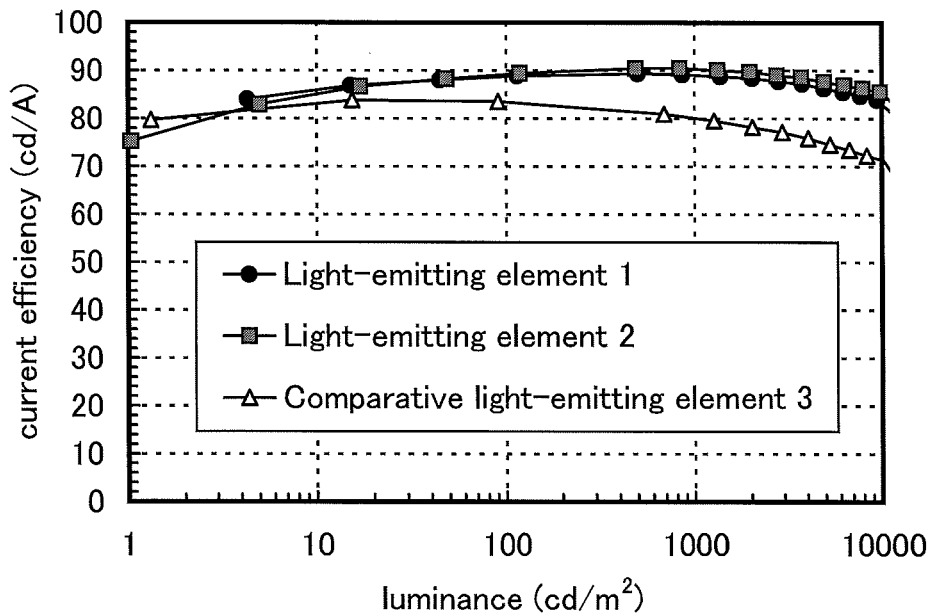
FIG. 13 is a graph showing current efficiency-luminance characteristics of the light-emitting elements in Example 2.
Figure 14:
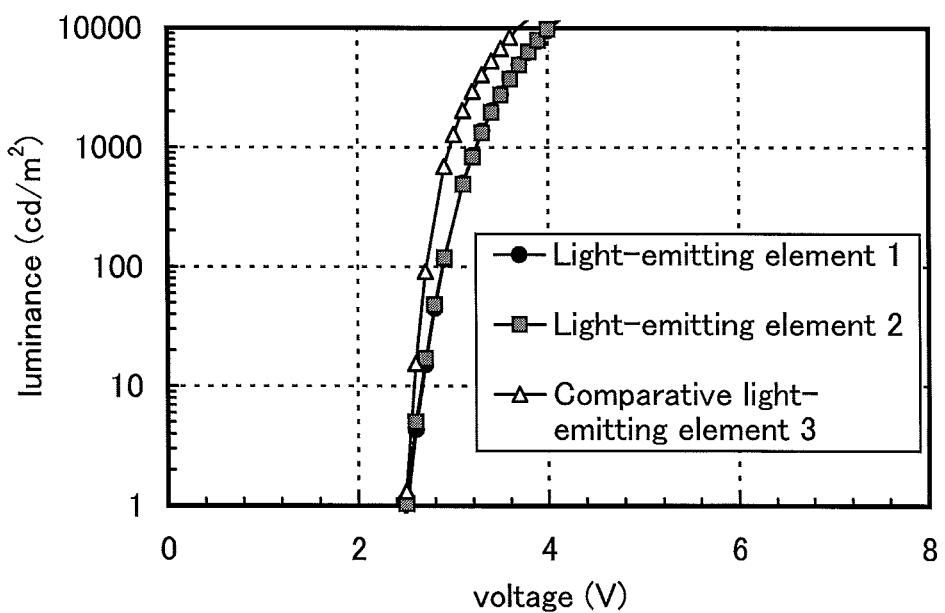
FIG. 14 is a graph showing luminance-voltage characteristics of the light-emitting elements in Example 2.
Figure 15:
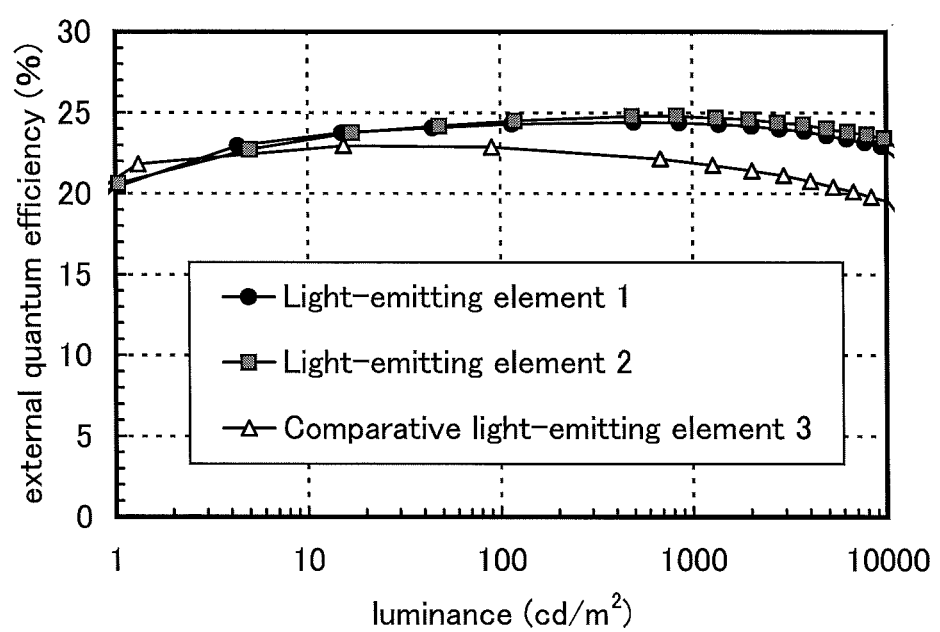
FIG. 15 is a graph showing external quantum efficiency-luminance characteristics of the light-emitting elements in Example 2.

FIG. 13 shows the current efficiency-luminance characteristics of Light-emitting element 1, Light-emitting element 2, and Comparative light-emitting element 3. In FIG. 13, the horizontal axis indicates luminance (cd/m$^2$) and the vertical axis indicates current efficiency (cd/A). FIG. 14 shows luminance-voltage characteristics of Light-emitting element 1, Light-emitting element 2, and Comparative light-emitting element 3. In FIG. 14, the horizontal axis indicates voltage (V) and the vertical axis indicates luminance (cd/m$^2$). FIG. 15 shows the external quantum efficiency-luminance characteristics of Light-emitting element 1, Light-emitting element 2, and Comparative light-emitting element 3. In FIG. 15, the horizontal axis indicates luminance (cd/m$^2$) and the vertical axis indicates external quantum efficiency (%).

Table 2 shows the voltage (V), current density (mA/cm$^2$), CIE chromaticity coordinates (x, y), current efficiency (cd/A), and external quantum efficiency (%) of each light-emitting element at a luminance of around 1000 cd/m$^2$.

The current efficiency and external quantum efficiency of Light-emitting element 1 at a luminance of 859 cd/m$^2$ were 89 cd/A and 24%, respectively. The current efficiency and external quantum efficiency of Light-emitting element 2 at a luminance of 831 cd/m$^2$ were 90 cd/A and 25%, respectively. The current efficiency and external quantum efficiency of Comparative light-emitting element 3 at a luminance of 1277 cd/m$^2$ were 79 cd/A and 22%, respectively.

Thus, the above results indicate that that Light-emitting element 1 and Light-emitting element 2, which are each one embodiment of the present invention, can have higher current efficiency than Comparative light-emitting element 3 by 10 cd/A to 11 cd/A. It is also indicated that Light-emitting element 1 and Light-emitting element 2, which are each one embodiment of the present invention, can have higher external quantum efficiency than Comparative light-emitting element 3 by 2% to 3%. Furthermore, as shown in FIG. 13 and FIG. 15, the emission efficiency and the external quantum efficiency of each of Light-emitting element 1 and Light-emitting element 2 become higher in a high luminance region than Comparative light-emitting element 3.

As described above, the organic compound of one embodiment of the present invention is used for the hole-transport layer of the light-emitting element of one embodiment of the present invention, so that high emission efficiency and high external quantum efficiency can be obtained. Therefore, the organic compound of one embodiment of the present invention is effective as a material used for the hole-transport layer of the light-emitting element.

TABLE 2

| | Voltage (V) | Current density (mA/cm$^2$) | CIE chromaticity coordinates | | Luminance (cd/m$^2$) | Current efficiency (cd/A) | External quantum efficiency (%) |
|---|---|---|---|---|---|---|---|
| | | | x | y | | | |
| Light-emitting element 1 | 3.2 | 1.0 | 0.43 | 0.56 | 859 | 89 | 24 |
| Light-emitting element 2 | 3.2 | 0.9 | 0.44 | 0.55 | 831 | 90 | 25 |
| Comparative light-emitting element 3 | 3.0 | 1.6 | 0.43 | 0.56 | 1277 | 79 | 22 |

As shown in Table 2, the CIE chromaticity coordinates of Light-emitting element 1 at a luminance of 859 cd/m$^2$ were (x, y)=(0.43, 0.56). The CIE chromaticity coordinates of Light-emitting element 2 at a luminance of 831 cd/m$^2$ were (x, y)=(0.44, 0.55). The CIE chromaticity coordinates of Comparative light-emitting element 3 at a luminance of 1277 cd/m$^2$ were (x, y)=(0.43, 0.56).

EXAMPLE 3

In this example, light-emitting elements (Light-emitting element 4 and Light-emitting element 5), which are each one embodiment of the present invention, will be described with reference to FIG. 12. Chemical formulae of materials used in this example are shown below.

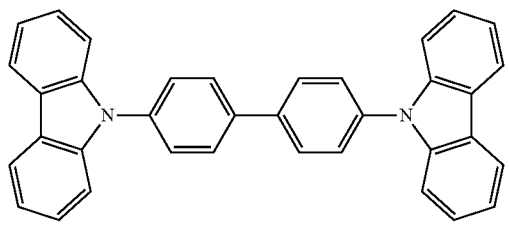

CBP

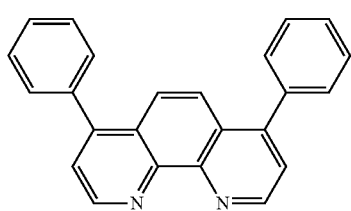

BPhen

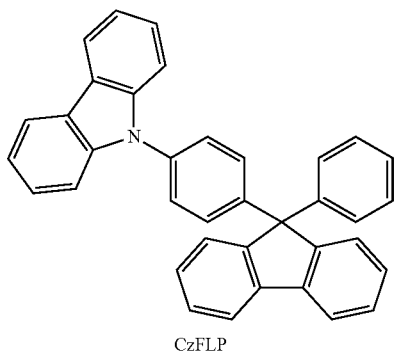

CzFLP

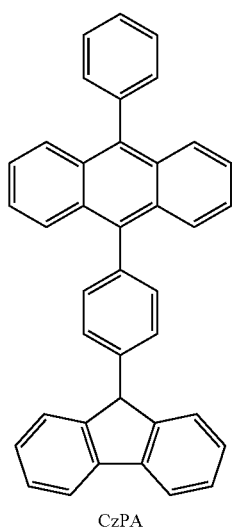

CzPA

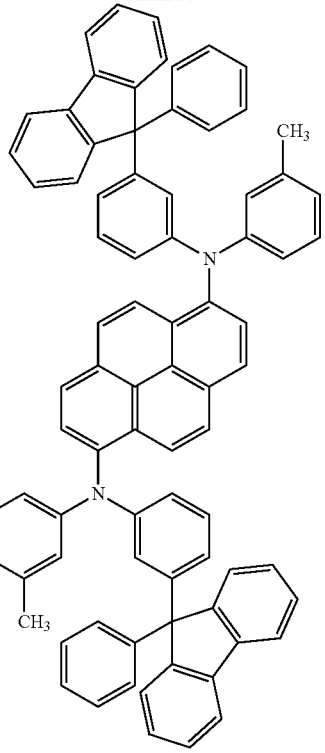

1,6mMemFLPAPm

Methods for manufacturing Light-emitting element 4 and Light-emitting element 5 of this example will be described below.

(Light-Emitting Element 4)

First, an indium oxide-tin oxide compound containing silicon or silicon oxide (ITO-SiO$_2$, hereinafter abbreviated to ITSO) was deposited by a sputtering method over the substrate 1100, whereby the first electrode 1101 was formed. Note that the composition ratio of In$_2$O$_3$ to SnO$_2$ and SiO$_2$ in the target used was 85:10:5 [wt %]. The thickness of the first electrode 1101 was 110 nm and the electrode area was 2 mm×2 mm. Here, the first electrode 1101 functions as an anode of the light-emitting element.

Next, as pretreatment for forming the light-emitting element over the substrate 1100, the surface of the substrate was washed, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus. Then, the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 4,4'-di(N-carbazolyl)biphenyl (abbreviation: CBP) and molybdenum oxide were co-evaporated by an evaporation method using resistance heating to form a hole-injection layer 1111 on the first electrode 1101. The thickness of the hole-injection layer 1111 was set to 50 nm, and the weight ratio of CBP to molybdenum oxide was adjusted to 2:1 (=CBP: molybdenum oxide).

Next, the hole-transport layer 1112 was formed over the hole-injection layer 1111 by evaporation of CzFLP (abbreviation) synthesized in Example 1. The thickness of the hole-transport layer 1112 was set to 10 nm.

Next, 9-[4-(10-phenyl-9-anthracenyl)phenyl]-9H-Carbazole (abbreviation: CzPA) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) were co-evaporated over the hole-transport layer 1112 to form a light-emitting layer 1113. Here, the weight ratio of CzPA (abbreviation) to 1,6mMemFLPAPrn (abbreviation) was adjusted to 1:0.04 (=CzPA:1,6mMemFLPAPrn). The thickness of the light-emitting layer 1113 was 30 nm.

Note that 1,6mMemFLPAPrn (abbreviation) is a fluorescent compound and used as a guest material in the light-emitting layer 1113.

Next, a film of CzPA (abbreviation) was formed to a thickness of 10 nm over the light-emitting layer 1113, whereby the first electron-transport layer 1114a was formed.

Next, a film of BPhen was formed to a thickness of 15 nm on the first electron-transport layer 1114a, whereby a second electron-transport layer 1114b was formed.

Next, a film of lithium fluoride (LiF) was formed to a thickness of 1 nm on the second electron-transport layer 1114b by evaporation, whereby an electron-injection layer 1115 was formed.

Lastly, a film of aluminum (Al) was formed to a thickness of 200 nm by evaporation, whereby a second electrode 1103 functioning as a cathode was formed. Thus, Light-emitting element 4 of this example was manufactured.

Note that, in the above evaporation process, evaporation was all performed by a resistance heating method.

(Light-Emitting Element 5)

The structure of Light-emitting element 5 is the same as that of Light-emitting element 4 except for the structure of the hole-transport layer 1112. Only the structure of Light-emitting element 5 which is different from that of Light-emitting element 4 is described below.

The hole-transport layer 1112 was formed over the hole-injection layer 1111 by evaporation of mCzFLP (abbreviation) synthesized in Example 1. The thickness of the hole-transport layer 1112 was set to 10 nm.

Table 3 shows element structures of Light-emitting Elements 4 and 5 formed as described above.

TABLE 3

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 4 | ITSO 110 nm | CBP:MoOx (=2:1) 50 nm | CzFLP 10 nm | CzPA:1,6mMemFLPAPrn (=1:0.04) 30 nm | CzPA 10 nm | BPhen 15 nm | LiF 1 nm | Al 200 nm |
| Light-emitting element 5 | ITSO 110 nm | CBP:MoOx (=2:1) 50 nm | mCzFLP 10 nm | CzPA:1,6mMemFLPAPrn (=1:0.04) 30 nm | CzPA 10 nm | BPhen 15 nm | LiF 1 nm | Al 200 nm |

In a glove box containing a nitrogen atmosphere, each of Light-emitting elements 4 and 5 was sealed with a glass substrate so as not to be exposed to the air (a sealant was applied onto an outer edge of the element and heat treatment was performed at 80° C. for one hour at the time of sealing). After that, operation characteristics of these light-emitting elements were measured. Note that the measurement was carried out at room temperature (in an atmosphere kept at 25° C.).

Figure 16:
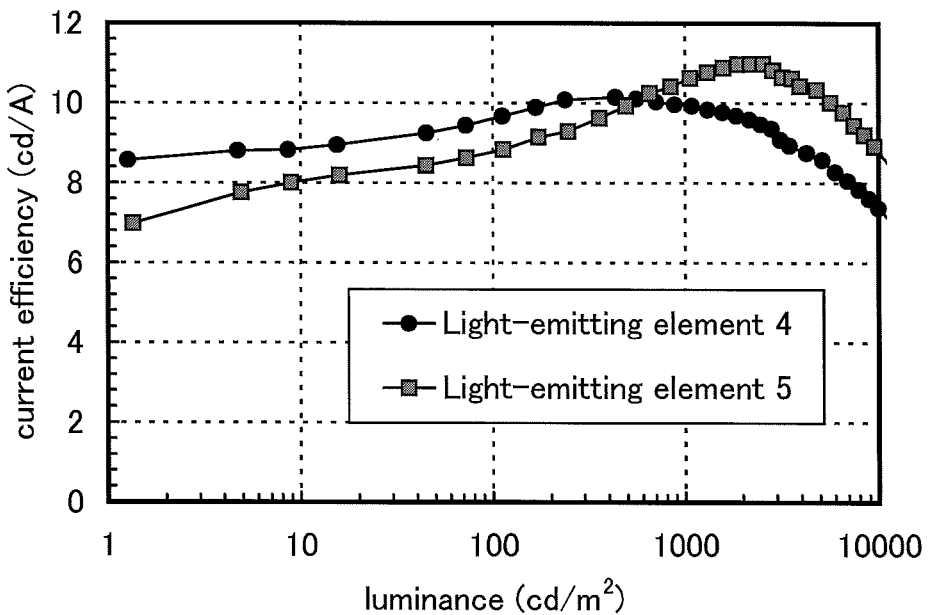
FIG. 16 is a graph showing current efficiency-luminance characteristics of the light-emitting elements in Example 3.
Figure 17:
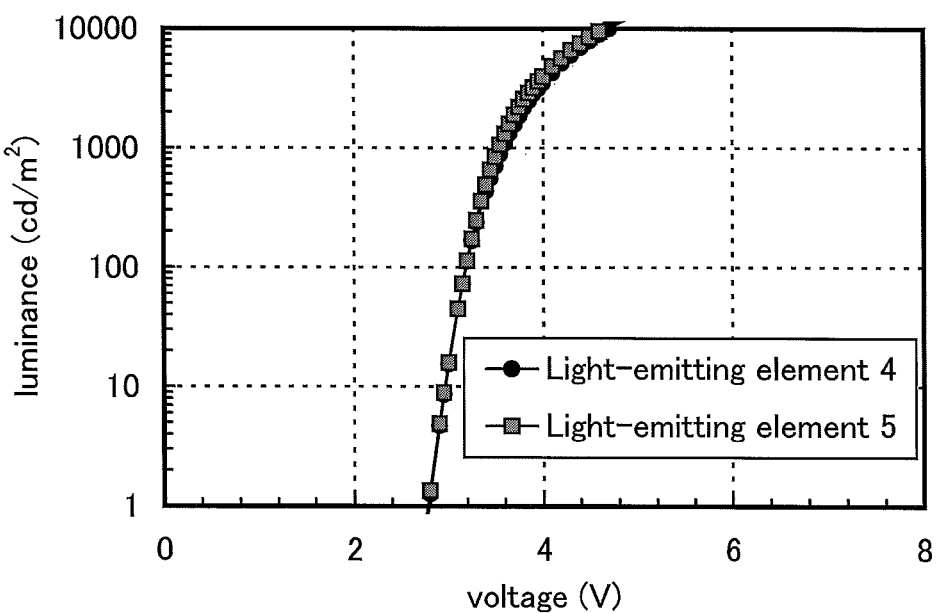
FIG. 17 is a graph showing luminance-voltage characteristics of the light-emitting elements in Example 3.
Figure 18:
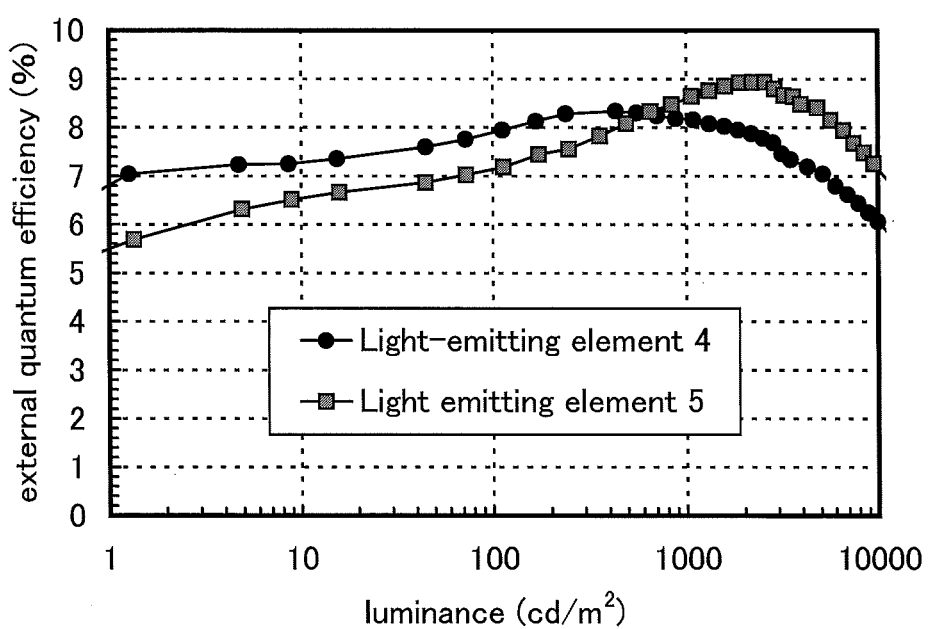
FIG. 18 is a graph showing external quantum efficiency-luminance characteristics of the light-emitting elements in Example 3.

FIG. 16 shows the current efficiency-luminance characteristics of Light-emitting element 4 and Light-emitting element 5. In FIG. 16, the horizontal axis indicates luminance (cd/m$^2$) and the vertical axis indicates current efficiency (cd/A). FIG. 17 shows luminance-voltage characteristics of Light-emitting element 4 and Light-emitting element 5. In FIG. 17, the horizontal axis indicates voltage (V) and the vertical axis indicates luminance (cd/m$^2$). FIG. 18 shows the external quantum efficiency-luminance characteristics of Light-emitting element 4 and Light-emitting element 5. In FIG. 18, the horizontal axis indicates luminance (cd/m$^2$) and the vertical axis indicates external quantum efficiency (%).

Table 4 shows the voltage (V), current density (mA/cm$^2$), CIE chromaticity coordinates (x, y), current efficiency (cd/A), and external quantum efficiency (%) of each light-emitting element at a luminance of around 1000 cd/m$^2$.

TABLE 4

| | Voltage (V) | Current density (mA/cm$^2$) | CIE chromaticity coordinates x | CIE chromaticity coordinates y | Luminance (cd/m$^2$) | Current efficiency (cd/A) | External quantum efficiency (%) |
|---|---|---|---|---|---|---|---|
| Light-emitting element 4 | 3.6 | 11.0 | 0.14 | 0.17 | 1087 | 10 | 8 |
| Light-emitting element 5 | 3.6 | 10.0 | 0.14 | 0.17 | 1064 | 11 | 9 |

As shown in Table 4, the CIE chromaticity coordinates of Light-emitting element 4 at a luminance of 1087 cd/m$^2$ were (x, y)=(0.14, 0.17). The CIE chromaticity coordinates of Light-emitting element 5 at a luminance of 1064 cd/m$^2$ were (x, y)=(0.14, 0.17).

The current efficiency and external quantum efficiency of Light-emitting element 4 at a luminance of 1087 cd/m$^2$ were 10 cd/A and 8%, respectively. The current efficiency and external quantum efficiency of Light-emitting element 5 at a luminance of 1064 cd/m² were 11 cd/A and 9%, respectively.

The above indicates that Light-emitting element 4 and Light-emitting element 5, which are each one embodiment of the present invention, are elements having high current efficiency and high external quantum efficiency.

Figure 19:
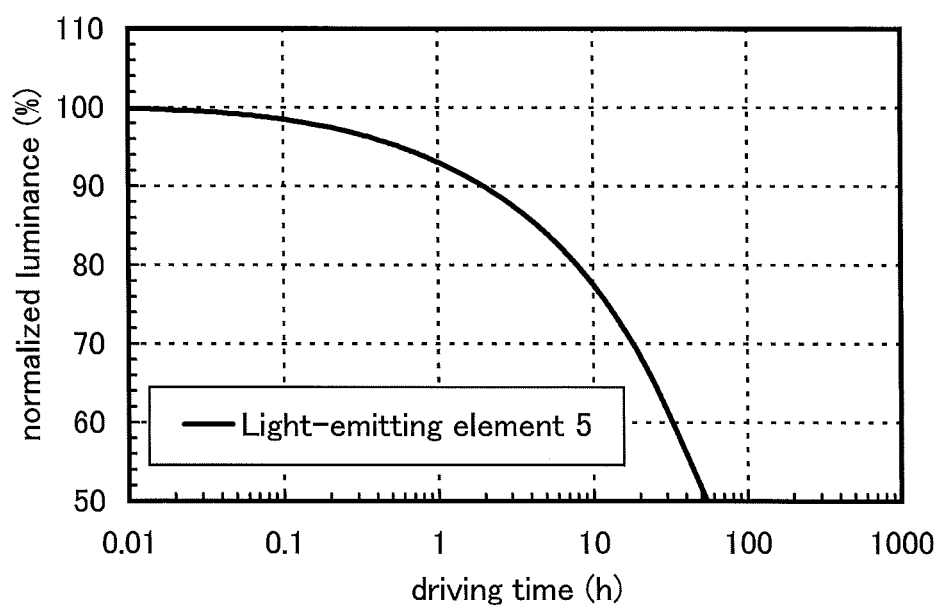
FIG. 19 is a graph showing the results of a reliability test of Light-emitting element 5.

Next, a reliability test was performed on Light-emitting element 5. FIG. 19 shows results of the reliability test.

In the reliability test, Light-emitting element 5 was driven under the conditions where the initial luminance was 5000 cd/m² and the current density was constant. The results are shown in FIG. 19. The horizontal axis indicates driving time (h) of the element and the vertical axis indicates normalized luminance (%) on the assumption that the initial luminance is 100%. According to FIG. 19, it takes 54 hours for the normalized luminance of Light-emitting element 5 to fall below 50%.

FIG. 19 shows that Light-emitting element 5 of one embodiment of the present invention has a long lifetime.

As described above, the organic compound of one embodiment of the present invention is used for the hole-transport layer of the light-emitting element of one embodiment of the present invention, so that high emission efficiency and high external quantum efficiency can be obtained. Therefore, the organic compound of one embodiment of the present invention is effective as a material used for the hole-transport layer of the light-emitting element. The organic compound of one embodiment of the present invention is a useful material also in a hole-transport layer of a light-emitting layer where a fluorescent compound is used as a guest material.

EXAMPLE 4

Figure 20:
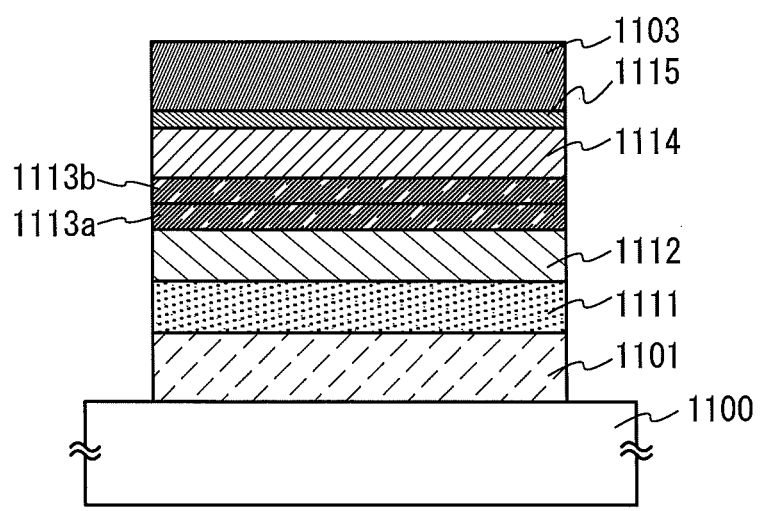
FIG. 20 illustrates each of light-emitting elements in Example 4.

In this example, a light-emitting element of one embodiment of the present invention (Light-emitting element 6) and a light-emitting element for comparison (Comparative light-emitting element 7) will be described with reference to FIG. 20. Chemical formulae of materials used in this example are shown below.

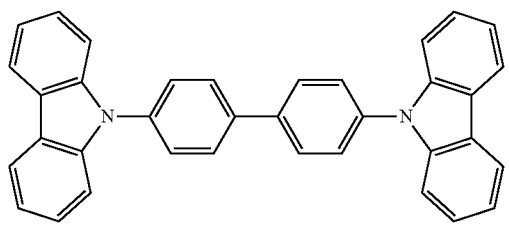
CBP

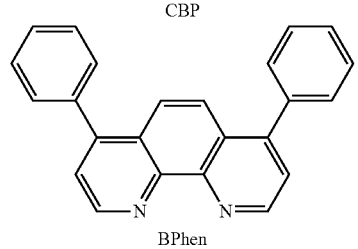
BPhen

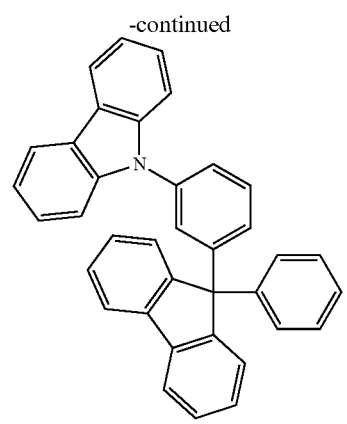
mCzFLP

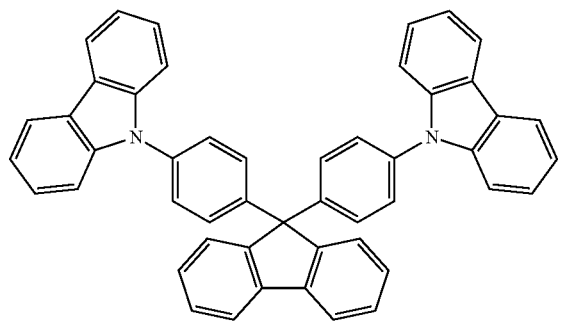
Cz2FLP

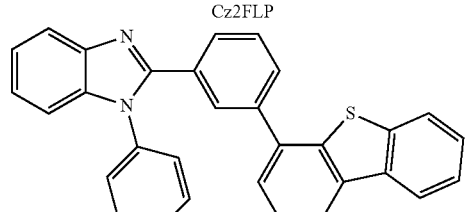
mDBTBIm-II

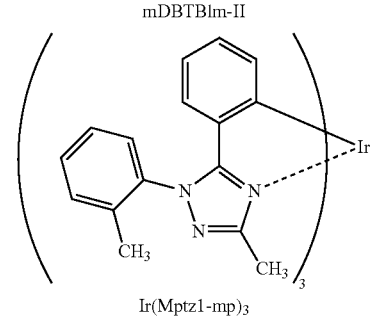
Ir(Mptz1-mp)₃

Methods for manufacturing Light-emitting element 6 and Comparative light-emitting element 7 of this example will be described.

(Light-Emitting Element 6)

First, an indium oxide-tin oxide compound containing silicon or silicon oxide (ITO-SiO$_2$, hereinafter abbreviated to ITSO) was deposited by a sputtering method over a substrate 1100, whereby a first electrode 1101 was formed. Note that the composition ratio of In$_2$O$_3$ to SnO$_2$ and SiO$_2$ in the target used was 85:10:5 [wt %]. The thickness of the first electrode 1101 was 110 nm and the electrode area was 2 mm×2 mm. Here, the first electrode 1101 functions as an anode of the light-emitting element.

Next, as pretreatment for forming the light-emitting element over the substrate 1100, the surface of the substrate was washed, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus. Then, the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, CBP (abbreviation) and molybdenum oxide were co-evaporated by an evaporation method using resistance heating to form a hole-injection layer 1111 on the first electrode 1101. The thickness of the hole-injection layer 1111 was set to 60 nm, and the weight ratio of CBP to molybdenum oxide was adjusted to 2:1 (=CBP:molybdenum oxide).

Next, the hole-transport layer 1112 was formed over the hole-injection layer 1111 by evaporation of mCzFLP (abbreviation) synthesized in Example 1. The thickness of the hole-transport layer 1112 was set to 10 nm.

Next, mCzFLP (abbreviation) and tris[3-methyl-1-(2-methylphenyl)-5-phenyl-1H-1,2,4-triazolato]iridium(III) (abbreviation: Ir(Mptz 1-mp)$_3$) were co-evaporated over the hole-transport layer 1112 to form a first light-emitting layer 1113a. Here, the weight ratio of mCzFLP (abbreviation) to Ir(Mptz1-mp)$_3$ (abbreviation) was set to 1:0.08 (=mCzFLP:Ir(Mptz1-mp)$_3$). The thickness of the first light-emitting layer 1113a was set to 30 nm.

Then, 2-[3-(dibenzothiophen-4-yl)phenyl]-1-phenyl-1H-benzimidazole (abbreviation: mDBTBIm-II) and Ir(Mptz 1-mp)$_3$ (abbreviation) were co-evaporated over the first light-emitting layer 1113a to form a second light-emitting layer 1113b. Here, the weight ratio of mDBTBIm-II (abbreviation) to Ir(Mptz 1-mp)$_3$ (abbreviation) was adjusted to 1:0.08 (=mDBTBIm-II:Ir(Mptz 1-mp)$_3$). The thickness of the second light-emitting layer 1113b was set to 10 nm.

Next, a film of BPhen (abbreviation) was formed to a thickness of 15 nm on the second light-emitting layer 1113b, whereby the electron-transport layer 1114 was formed.

Next, a film of lithium fluoride (LiF) was formed to a thickness of 1 nm over the electron-transport layer 1114 by evaporation, whereby an electron-injection layer 1115 was formed.

Lastly, a film of aluminum (Al) was formed to a thickness of 200 nm by evaporation, whereby a second electrode 1103 functioning as a cathode was formed. Thus, Light-emitting element 6 of this example was manufactured.

Note that, in the above evaporation process, evaporation was all performed by a resistance heating method.

(Comparative Light-Emitting Element 7)

The structure of Comparative light-emitting element 7 is the same as that of Light-emitting element 6 except for the structures of the hole-transport layer 1112 and the first light-emitting layer 1113a. Only the structure of Comparative light-emitting element 7 which is different from that of Light-emitting element 6 is described below.

The hole-transport layer 1112 was formed over the hole-injection layer 1111 by evaporation of 9,9'-(9H-fluorene-9,9-diyldi-4,1-phenylene)bis(9H-carbazole) (abbreviation: Cz2FLP). The thickness of the hole-transport layer 1112 was set to 10 nm.

Next, Cz2FLP (abbreviation) and Ir(Mptz 1-mp)$_3$ (abbreviation) were co-evaporated over the hole-transport layer 1112 to form the first light-emitting layer 1113a. Here, the weight ratio of Cz2FLP (abbreviation) to Ir(Mptz 1-mp)$_3$ (abbreviation) was set to 1:0.15 (=Cz2FLP:Ir(Mptz1-mp)$_3$). The thickness of the first light-emitting layer 1113a was set to 30 nm.

Table 5 shows element structures of Light-emitting element 6 and Comparative light-emitting element 7 formed as described above.

TABLE 5

| | First electrode | Hole-injection layer | Hole-transport layer | First light-emitting layer | Second light-emitting layer | Electron-transport layer | Electron-injection layer | Second electrode |
|---|---|---|---|---|---|---|---|---|
| Light-emitting element 6 | ITSO 110 nm | CBP:MoOx (=2:1) 60 nm | mCzFLP 10 nm | mCzFLP:Ir(Mptz1-mp)$_3$ (=1:0.08) 30 nm | mDBTBIm-II:Ir(Mptz1-mp)$_3$ (=1:0.08) 10 nm | BPhen 15 nm | LiF 1 nm | Al 200 nm |
| Comparative light-emitting element 7 | ITSO 110 nm | CBP:MoOx (=2:1) 60 nm | Cz2FLP 10 nm | Cz2FLP:Ir(Mptz1-mp)$_3$ (=1:0.15) 30 nm | mDBTBIm-II:Ir(Mptz1-mp)$_3$ (=1:0.08) 10 nm | BPhen 15 nm | LiF 1 nm | Al 200 nm |

In a glove box containing a nitrogen atmosphere, each of Light-emitting element 6 and Comparative light-emitting element 7 was sealed with a glass substrate so as not to be exposed to the air (a sealant was applied onto an outer edge of the element and heat treatment was performed at 80° C. for one hour at the time of sealing). After that, operation characteristics of these light-emitting elements were measured. Note that the measurement was carried out at room temperature (in an atmosphere kept at 25° C.).

Figure 21:
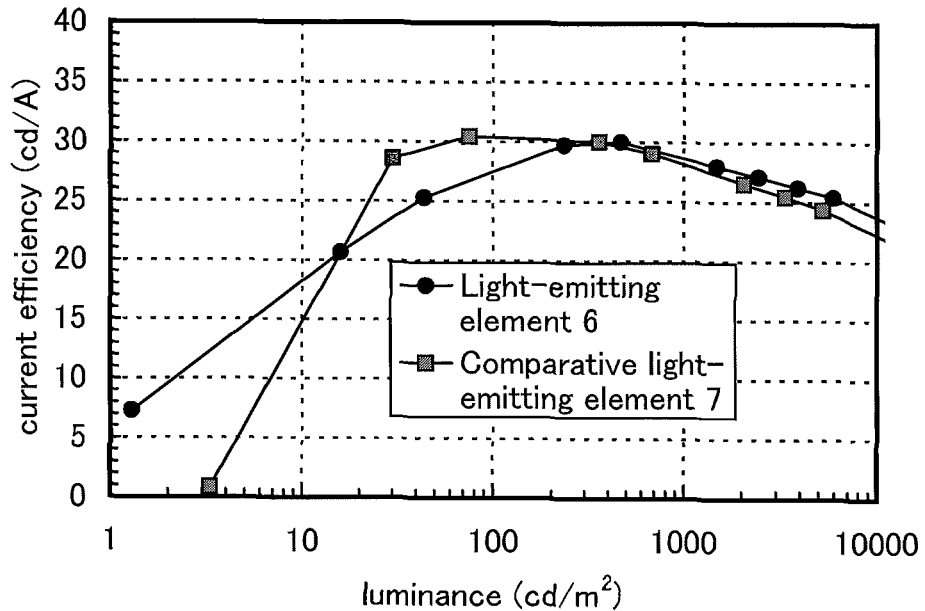
FIG. 21 is a graph showing current efficiency-luminance characteristics of the light-emitting elements in Example 4.
Figure 22:
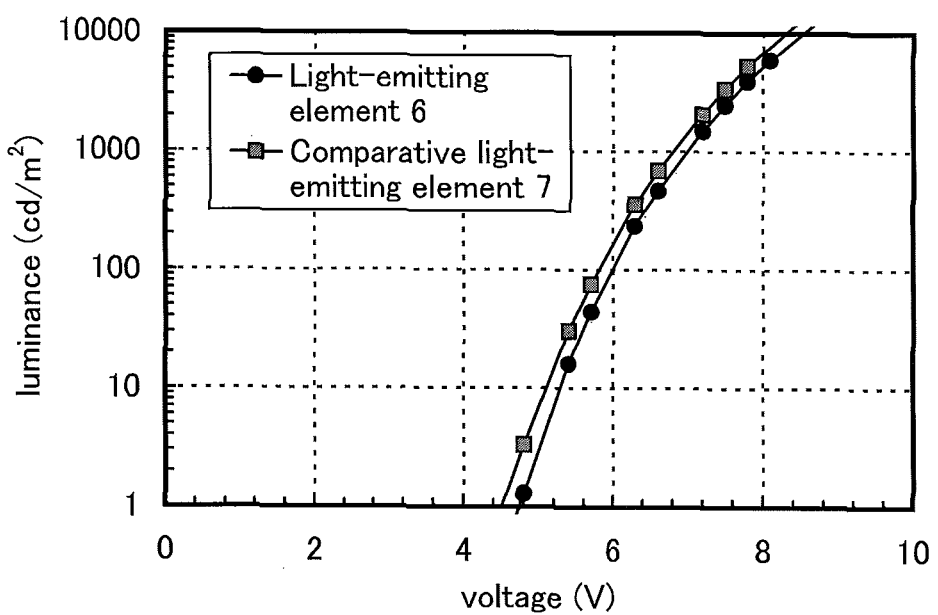
FIG. 22 is a graph showing luminance-voltage characteristics of the light-emitting elements in Example 4.
Figure 23:
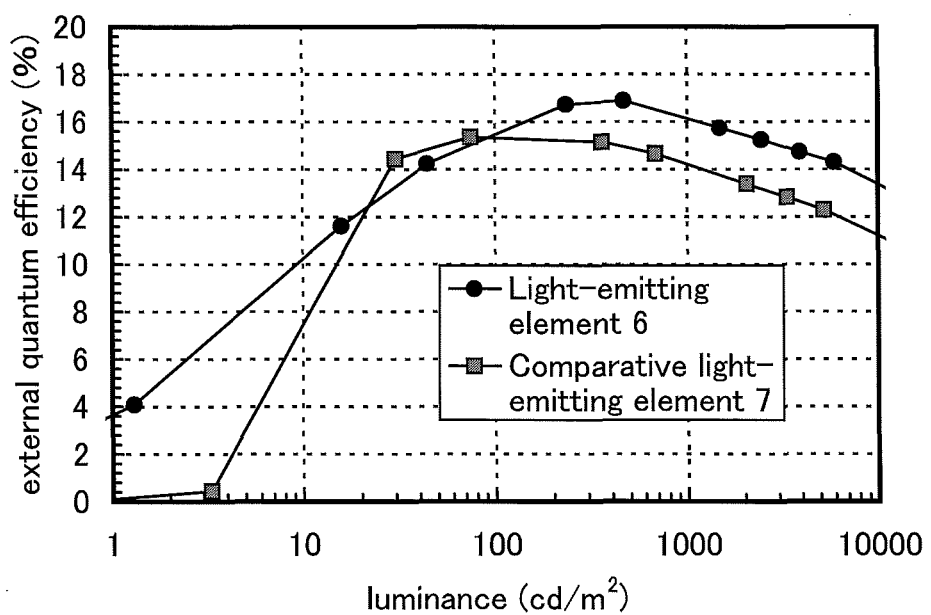
FIG. 23 is a graph showing external quantum efficiency-luminance characteristics of the light-emitting elements in Example 4.

FIG. 21 shows the current efficiency-luminance characteristics of Light-emitting element 6 and Comparative light-emitting element 7. In FIG. 21, the horizontal axis indicates luminance (cd/m$^2$) and the vertical axis indicates current efficiency (cd/A). FIG. 22 shows luminance-voltage characteristics of Light-emitting element 6 and Comparative light-emitting element 7. In FIG. 22, the horizontal axis indicates voltage (V) and the vertical axis indicates luminance (cd/m$^2$). FIG. 23 shows the external quantum efficiency-luminance characteristics of Light-emitting element 6 and Comparative light-emitting element 7. In FIG. 23, the horizontal axis indicates luminance (cd/m$^2$) and the vertical axis indicates external quantum efficiency (%).

Table 6 shows the voltage (V), current density (mA/cm$^2$), CIE chromaticity coordinates (x, y), current efficiency (cd/A), and external quantum efficiency (%) of each light-emitting element at a luminance of around 500 cd/m$^2$.

TABLE 6

|  | Voltage (V) | Current density (mA/cm$^2$) | CIE chromaticity coordinates x | CIE chromaticity coordinates y | Luminance (cd/m$^2$) | Current efficiency (cd/A) | External quantum efficiency (%) |
|---|---|---|---|---|---|---|---|
| Light-emitting element 6 | 6.6 | 1.5 | 0.17 | 0.27 | 463 | 30 | 17 |
| Comparative light-emitting element 7 | 6.6 | 2.3 | 0.18 | 0.32 | 681 | 29 | 15 |

As shown in Table 6, the CIE chromaticity coordinates of Light-emitting element 6 at a luminance of 463 cd/m$^2$ were (x, y)=(0.17, 0.27). The CIE chromaticity coordinates of Comparative light-emitting element 7 at a luminance of 681 cd/m$^2$ were (x, y)=(0.18, 0.32).

The current efficiency and external quantum efficiency of Light-emitting element 6 at a luminance of 463 cd/m$^2$ were 30 cd/A and 17%, respectively. The current efficiency and external quantum efficiency of Comparative light-emitting element 7 at a luminance of 681 cd/m$^2$ were 29 cd/A and 15%, respectively.

The above indicates that Light-emitting element 6 of one embodiment of the present invention has current efficiency and external quantum efficiency substantially the same as those of Comparative light-emitting element 7. In addition, light emission derived from a dopant was observed from Light-emitting element 6 and it was found that Light-emitting element 6 is a light-emitting element with high color purity as compared to Comparative light-emitting element 7.

Figure 24:
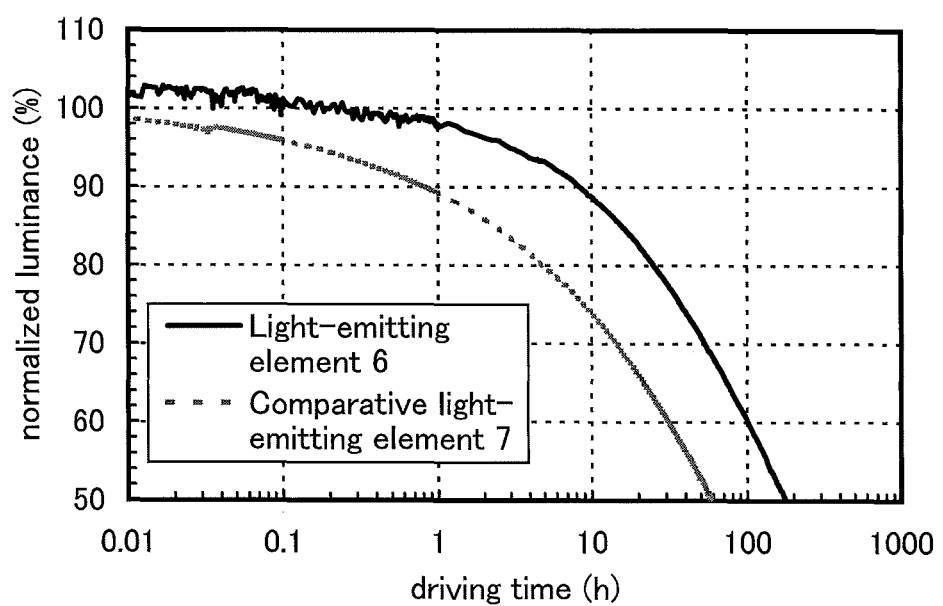
FIG. 24 is a graph showing the results of reliability tests of Light-emitting element 6 and Comparative light-emitting element 7.

Next, a reliability test was performed on each of Light-emitting element 6 and Comparative light-emitting element 7. FIG. 24 shows results of the reliability tests.

In the reliability test, each light-emitting element was driven under the conditions where the initial luminance was 5000 cd/m$^2$ and the current density was constant. The results are shown in FIG. 24. The horizontal axis indicates driving time (h) of the element and the vertical axis indicates normalized luminance (%) on the assumption that the initial luminance is 100%. According to FIG. 24, it takes 178 hours for the normalized luminance of Light-emitting element 6 to fall below 50% and it takes 56 hours for the normalized luminance of Comparative light-emitting element 7 to fall below 50%.

FIG. 24 shows that Light-emitting element 6 of one embodiment of the present invention has a long lifetime as compared to Comparative light-emitting element 7. This is because Light-emitting element 6 of one embodiment of the present invention has a relatively high T1 level as compared to Comparative light-emitting element 7.

As described above, the organic compound of one embodiment of the present invention is used for a hole-transport layer and a light-emitting layer of the light-emitting element of one embodiment of the present invention, so that a highly reliable light-emitting element can be achieved. Therefore, the organic compound of one embodiment of the present invention is effective as a material used for the hole-transport layer and the light-emitting layer of the light-emitting element.

This application is based on Japanese Patent Application serial no. 2012-096888 filed with Japan Patent Office on Apr. 20, 2012, the entire contents of which are hereby incorporated by reference.

What is claimed is:

1. A light-emitting element comprising:
   a hole-transport layer and a light-emitting layer between a pair of electrodes,
   wherein at least one of the hole-transport layer and the light-emitting layer includes an organic compound having a skeleton represented by a formula (G1),

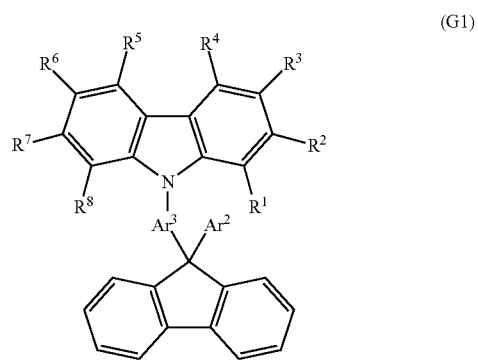

(G1)

wherein:
   $Ar^2$ is any one of an unsubstituted phenyl group, an unsubstituted biphenyl group, and a group having 3 to 6 benzene rings which are bonded at meta-positions;
   $Ar^3$ is any one if a phenylene group, a biphenyldiyl group, and an arylene group having 3 to 6 rings which are bonded at meta-positions; and
   $R^1$ to $R^8$ are each independently any one of hydrogen, an alkyl group having 1 to 12 carbon atoms, a substituted or unsubstituted phenyl group, and a substituted or unsubstituted biphenyl group.

2. The light-emitting element according to claim 1,
   wherein $Ar^2$ is a phenyl group or a biphenyl group, and
   wherein $Ar^3$ is a phenylene group or a biphenyldiyl group.

3. The light-emitting element according to claim 2, wherein $Ar^3$ is a metaphenylene group or a biphenyl-3,3'-diyl group.

4. A light-emitting device comprising the light-emitting element according to claim 1.

5. An electronic device comprising the light-emitting device according to claim 4.

6. A lighting device comprising the light-emitting device according to claim 4.

7. An organic compound represented by a formula (G1),

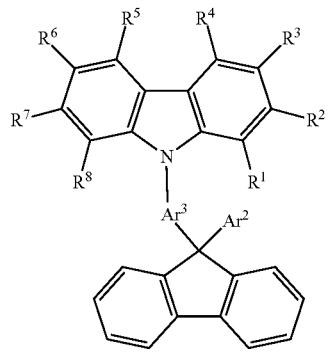
(G1)

wherein:

Ar² is any one of an unsubstituted phenyl group, an unsubstituted biphenyl group, and a group having 3 to 6 benzene rings which are bonded at meta-positions;

Ar³ is any one of a phenylene group, a biphenyldiyl group, and an arylene group having 3 to 6 benzene rings which are bonded at meta-positions; and R¹ to R⁸ are each independently any one of hydrogen, an alkyl group having 1 to 12 carbon atoms, a substituted or unsubstituted phenyl group, and a substituted or unsubstituted biphenyl group.

8. The organic compound according to claim 7,
wherein Ar² is a phenyl group or a biphenyl group, and
wherein Ar³ is a phenylene group or a biphenyldiyl group.

9. The organic compound according to claim 8, wherein Ar³ is a metaphenylene group or a biphenyl-3,3'-diyl group.

10. The organic compound according to claim 7, wherein the organic compound is represented by a formula (G2-1)

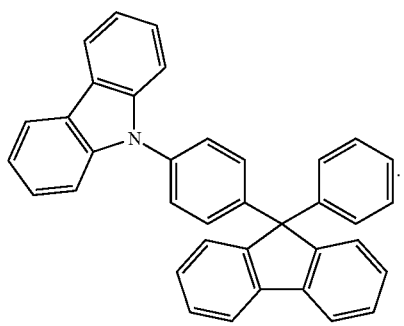
(G2-1)

11. The organic compound according to claim 7, wherein the organic compound is represented by a formula (G2-2)

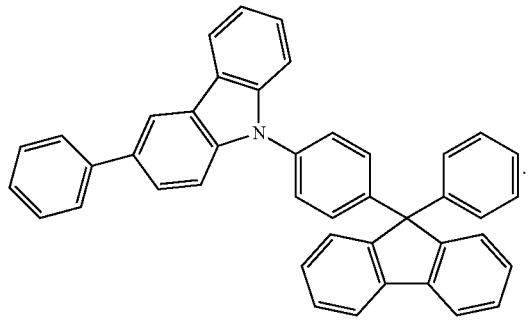
(G2-2)

12. The organic compound according to claim 7, wherein the organic compound is represented by a formula (G3)

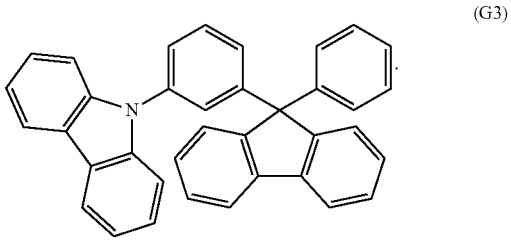 [SMILES: c1ccc(C2(c3cccc(-n4c5ccccc5c5ccccc54)c3)c3ccccc3-c3ccccc32)cc1]
(G3)

13. An organic compound represented by a formula (G1),

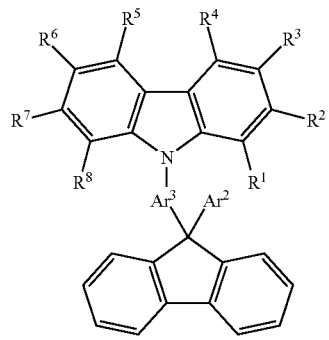
(G1)

wherein:

Ar² is an unsubstituted phenyl group or an unsubstituted biphenyl group;

Ar³ is any one of a phenylene group, a biphenyldiyl group, and an arylene group having 3 to 6 benzene rings which are bonded at meta-postions; and R¹ to R⁸ are each independently any one of hydrogen, an alkyl group having 1 to 12 carbon atoms, a substituted or unsubstituted phenyl group, and a substituted or unsubstituted biphenyl group.

14. The organic compound according to claim 13, wherein Ar³ is a phenylene group or a biphenyldiyl group.

15. The organic compound according to claim 14, wherein Ar³ is a metaphenylene group or a biphenyl-3,3'-diyl group.

* * * * *

UNITED STATES PATENT AND TRADEMARK OFFICE
CERTIFICATE OF CORRECTION

PATENT NO. : 9,882,138 B2
APPLICATION NO. : 13/860055
DATED : January 30, 2018
INVENTOR(S) : Harue Osaka et al.

It is certified that error appears in the above-identified patent and that said Letters Patent is hereby corrected as shown below:

In the Claims

-- Claim 1, Column 60, Line 46: change "if" to --of--;

-- Claim 10, Column 61, Line 53, formula (G2-1): delete the "." outside of the upper right ring and change the "." to as follows:

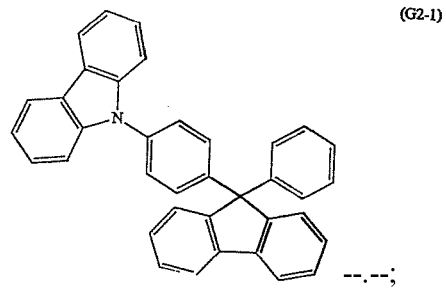

-- Claim 11, Column 62, Line 9, formula (G2-2): delete the "." outside of the upper right ring and change the "." to as follows:

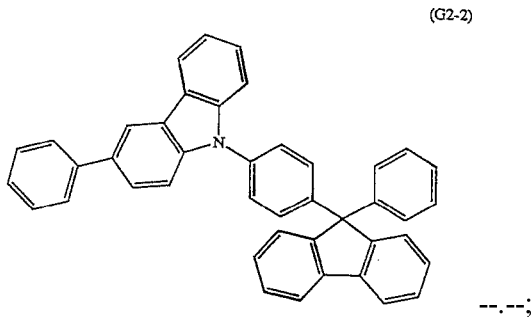

Signed and Sealed this
Seventeenth Day of April, 2018

Andrei Iancu
*Director of the United States Patent and Trademark Office*

-- Claim 12, Column 62, Line 23, formula (G3): delete the "." outside of the upper right ring and change the "." to as follows:
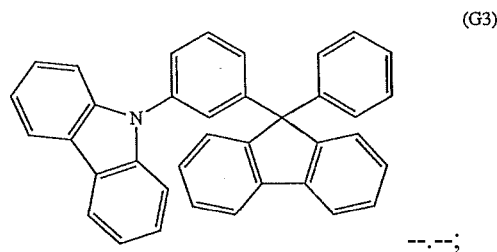
(G3)
--.--;
-- Claim 13, Column 62, Line 54, change "meta-postions" to --meta-positions--.